(12) United States Patent
King et al.

(10) Patent No.: US 10,633,591 B2
(45) Date of Patent: Apr. 28, 2020

(54) FLAME RETARDANT ITACONIC ACID-BASED COMPOUNDS

(71) Applicant: International Business Machines Corporation, Armonk, NY (US)

(72) Inventors: Scott B. King, Rochester, MN (US); Brandon M. Kobilka, Tucson, AZ (US); Joseph Kuczynski, North Port, FL (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 63 days.

(21) Appl. No.: 15/726,107

(22) Filed: Oct. 5, 2017

(65) Prior Publication Data

US 2019/0106633 A1 Apr. 11, 2019

(51) Int. Cl.
*C09K 21/14* (2006.01)
*C08K 5/5317* (2006.01)
(Continued)

(52) U.S. Cl.
CPC ............ *C09K 21/14* (2013.01); *C07C 29/147* (2013.01); *C07C 29/56* (2013.01); *C07C 51/353* (2013.01); *C07C 55/10* (2013.01); *C07F 9/4084* (2013.01); *C08G 18/638* (2013.01); *C08K 3/016* (2018.01); *C08K 3/32* (2013.01); *C08K 5/5313* (2013.01); *C08K 5/5317* (2013.01); *C08L 23/12* (2013.01); *C08L 31/06* (2013.01); *C09K 21/04* (2013.01); *C08K 5/0066* (2013.01)

(58) Field of Classification Search
CPC ........ C09K 21/14; C09K 21/04; C08K 3/016; C08K 5/0066; C08K 3/32; C08G 18/638; C08L 31/06; C08L 23/12; C07C 55/10
See application file for complete search history.

(56) References Cited

U.S. PATENT DOCUMENTS

2017/0107375 A1  4/2017  Pfaendner et al.

FOREIGN PATENT DOCUMENTS

CN  103965245 A  8/2014
WO  2014/105669 A1  7/2014

OTHER PUBLICATIONS

Ma et al., "Research progress on bio-based thermosetting resins," Polymer International, 2015, 11 pages, published online in Wiley Online Library. DOI: 10.1002/pi.5027.

Ma et al., "Synthesis and properties of phosphorus-containing bio-based epoxy resin from itaconic acid," Science China—Chemistry, Mar. 2014, vol. 57, No. 3, pp. 379-388, Science China Press and Springer-Verlag Berline Heidelberg. DOI: 10.1007/s11426-013-5025-3.

(Continued)

*Primary Examiner* — Andrew J. Oyer
(74) *Attorney, Agent, or Firm* — Kelsey M. Skodie

(57) ABSTRACT

A flame retardant itaconic acid-based compound, a process for forming a flame retardant polymer, and an article of manufacture comprising a material that contains a flame retardant itaconic acid-based polymer are disclosed. The flame retardant itaconic acid-based compound has variable moieties, which include methylene bridge groups, carbonyl groups, vinyl groups, functionalized groups, phenyl-substituted flame retardant groups, and/or functionalized flame retardant groups. The process for forming the flame retardant polymer includes forming a phosphorus-based flame retardant molecule, forming an itaconic acid derivative, chemically reacting the phosphorus-based flame retardant molecule and the itaconic acid derivative to form a flame retardant itaconic acid-based compound, and incorporating the itaconic acid-based flame retardant compound into a polymer to form the flame retardant polymer.

3 Claims, 23 Drawing Sheets

(51) Int. Cl.
*C08K 5/5313* (2006.01)
*C07C 29/147* (2006.01)
*C07F 9/40* (2006.01)
*C07C 51/353* (2006.01)
*C07C 29/56* (2006.01)
*C08K 3/016* (2018.01)
*C08K 3/32* (2006.01)
*C07C 55/10* (2006.01)
*C08L 23/12* (2006.01)
*C08L 31/06* (2006.01)
*C08K 5/00* (2006.01)
*C09K 21/04* (2006.01)
*C08G 18/63* (2006.01)

(56) References Cited

OTHER PUBLICATIONS

Specialchem, "Agreement for Production of Bio-based Polymers—AkzoNobel and Itaconix," Industry News, Feb. 7, 2017, (printed: May 25, 2017), pp. 1-3. http://adhesives.specialchem.com/news/industry-news/akzonobel-itaconix-sign-jda-000185726?lr=ias1702385&li=50001003&m_i=%2B9RYvHr2cuBqbg2Rp7Sfa2ji0rUu0k_1w42d2yVw%2BVrw9JpyzbB1jspkbvte_WMCI7xBFc5tTb4AyD23ERGVoE7welEF%2Bz#utm_source=NL&utm_medium=EML&utm_campaign=ias1702385.

"Dimethyl acetals," Organic Chemistry Portal, (printed May 25, 2017), pp. 1-2, http://www.organic-chemistry.org/protectivegroups/carbonyl/dimethylacetals.htm.

200-2

212

216-1

216-3

216-5

216-6

216-7

216-2    216-4

R = functional group
$E^1$ = Ph-substituted thioether
$E^2$ = functionalized thioether
X = O or S $M^1$ = 216-1, 216-2, 216-3, or 216-4

$M^2$ = 216-3 or 216-4

$M^3$ = 216-3 or 216-4

$M^4$ = 216-7, 216-8, 216-9, 216-10, 216-11, 216-12

$M^5$ = 216-1, 216-2, 216-3, or 216-4

302

352  3-Mercaptopropionate 356  2-Mercaptoethanol

360  Cysteamine HCl

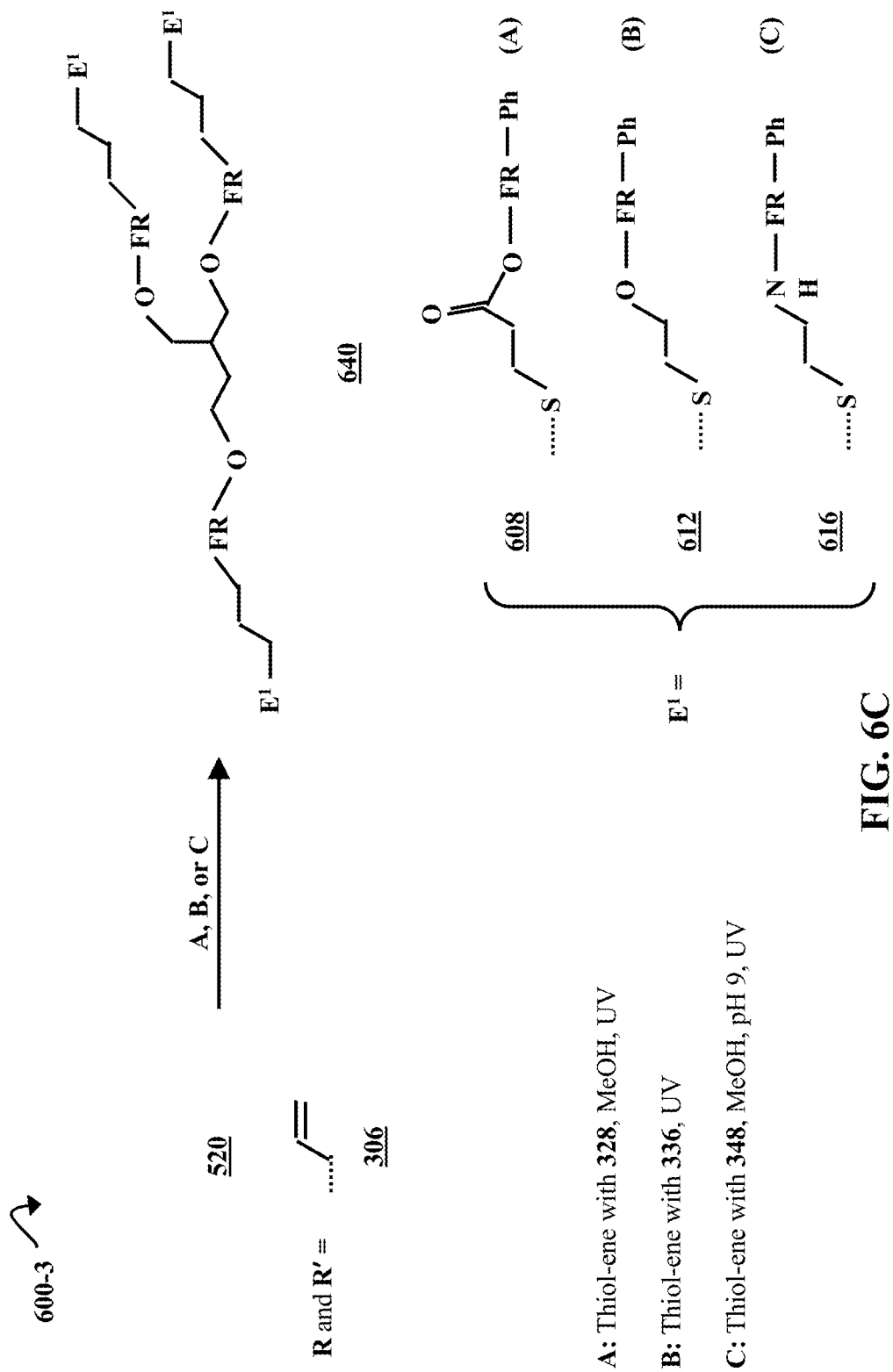

700

704

708

712

FLAME RETARDANT ITACONIC ACID-BASED COMPOUNDS

BACKGROUND

The present disclosure relates to bio-renewable flame retardant compounds and, more specifically, flame retardant itaconic acid-based compounds.

Bio-based, sustainable compounds can be used in the syntheses of substances that previously required petroleum-based raw materials. Examples of uses for bio-based compounds include polymers, flame retardants, cross-linkers, etc. There are numerous strategies for efficiently and inexpensively producing bio-based compounds on an industrial scale. Examples of these strategies can be found in fermentation technologies, membrane technologies, and genetic engineering. Itaconic acid (2-methylidenebutanedioic acid) is one example of a bio-based compound. Itaconic acid is produced by distillation of citric acid or by fermentation of carbohydrates, such as glucose or molasses.

SUMMARY

Various embodiments are directed to flame retardant itaconic acid-based compounds. The flame retardant itaconic acid-based compounds can have variable moieties, which can include a phenyl-substituted flame retardant group, an functionalized flame retardant group, a methylene bridge group, a carbonyl group, a vinyl group, and a functionalized group. The functionalized flame retardant group can have a functional group such as an allyl group, an epoxy group, a propylene carbonate group, a carboxylic acid group, a hydroxyl group, and an amine group. Further, the flame retardant groups can include phosphonyl and/or phosphoryl moieties. The flame retardant itaconic acid-based compound can be incorporated into a polymer to form a flame retardant polymer.

Additional embodiments are directed to a process of forming a flame retardant itaconic acid-based polymer. The flame retardant itaconic acid-based polymer can be produced by forming a phosphorus-based flame retardant molecule, forming an itaconic acid derivative, chemically reacting the phosphorus-based flame retardant molecule and the itaconic acid derivative to form a flame retardant itaconic acid-based compound, and incorporating the itaconic acid-based flame retardant compound into a polymer to form the flame retardant polymer. The itaconic acid derivative can be synthesized from itaconic acid that comes from a bio-based source. The phosphorus-based flame retardant molecule can be a phosphorus-based compound with allyl, epoxy, or phenyl groups. The flame retardant itaconic acid-based compound can have at least one functional group such as an allyl group, an epoxy group, a propylene carbonate group, a carboxylic acid group, an amine group, or a hydroxyl group. The flame retardant itaconic acid-based compound can also be reacted with lithium bromide and carbon dioxide. Additionally, the flame retardant itaconic acid-based compound can be incorporated into the polymer by blending, binding, or polymerizing.

Further embodiments are directed to an article of manufacture comprising a material that contains a flame retardant itaconic acid-based polymer. The article of manufacture can also contain an electronic component. Additionally, the material containing the flame retardant itaconic acid-based polymer can be a plastic for integrated circuit packing or an adhesive.

BRIEF DESCRIPTION OF THE DRAWINGS

FIG. 6C is a chemical reaction diagram illustrating a process of forming phenyl-substituted thioether-linked flame retardant 2-(hydroxymethyl)butane-1,4-diol-derived compounds, according to some embodiments of the present disclosure.

DETAILED DESCRIPTION

Figure 1:
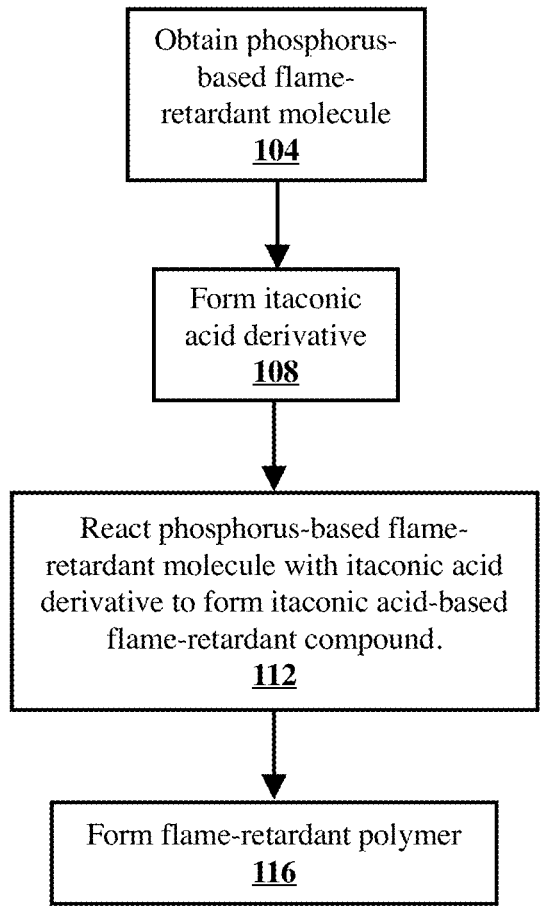
FIG. 1 is a flow diagram illustrating a process of forming an itaconic acid-based flame retardant polymer, according to some embodiments of the present disclosure.

Bio-based compounds are increasingly being used in the syntheses of substances that previously required petroleum-based raw materials. One benefit of bio-based compounds is that they are from renewable resources. Therefore, these compounds have applications in sustainable, or "green," materials. Sustainable materials are becoming more and more prevalent, due to the rising costs of fossil fuels and increasing environmental regulatory controls. Advances in biotechnology have provided numerous strategies for efficiently and inexpensively producing bio-based compounds on an industrial scale. Examples of these strategies can be found in fermentation technologies, membrane technologies, and genetic engineering. Biotechnological strategies can include plant-based and microorganism-based approaches. Plant-based approaches can involve obtaining a material directly from a plant, or growing plant tissues or cells that can produce bio-based compounds from various substrates using their own biosynthetic pathways. Microorganism-based approaches involve using native or genetically modified fungi, yeast, or bacteria to produce a desired compound from a structurally similar substrate.

Examples of uses for bio-based compounds include polymers, flame retardants, cross-linkers, etc. In some examples, bio-based polymers and petroleum-based polymers are blended to form a polymer composite. However, polymers can also be entirely bio-based, or produced from a combination of bio- and petroleum-based monomers. Bio-based compounds can impart flame retardant properties to bio- and petroleum-based polymers. For example, flame retardant molecules or cross-linkers can be incorporated into polymers. Additionally, flame retardant monomers can be polymerized to form flame retardant polymers.

Itaconic acid (2-methylidenebutanedioic acid) is one example of a bio-based compound that can have applications as a component of various polymers, resins, and monomers. Itaconic acid can be obtained by distillation of citric acid. Dry distillation of citric acid yields itaconic anhydride, which is hydrolyzed to itaconic acid. Itaconic acid can also be produced by the enzyme isocitrate lyase in bacteria such as *Salmonella enterica* or *Mycobacterium tuberculosis*. On an industrial scale, itaconic acid is commonly obtained via fermentation of carbohydrates, such as glucose and molasses, by fungi (e.g., *Aspergillus terreus* or *Ustilago maydis*).

According to the present disclosure, itaconic acid is used as a precursor for flame retardant compounds. These compounds can include small molecules, cross-linkers, monofunctional molecules, and monomers. The itaconic acid-based flame retardant compounds can be added to polymers, fabrics, resins, or other materials during blending, curing, foaming, extrusion, or other processing techniques. In addition to directly adding the itaconic acid-based flame retardant monomers to the materials during processing, the added itaconic acid-based flame retardant monomers can be contained within microcapsules.

FIG. 1 is a flow diagram illustrating a process 100 of forming a flame retardant polymer containing an itaconic acid-based flame retardant polymer, according to some embodiments of the present disclosure. Process 100 begins with the obtainment of a phosphorus-based flame retardant molecule. This is illustrated at step 104. The phosphorus-based flame retardant molecule has either a phosphoryl or a phosphonyl moiety (collectively referred to as an FR group) with an attached R functional group or phenyl (Ph) group. The R groups that are attached to the FR groups can vary, as is discussed in greater detail below. The phosphorus-based flame retardant molecules can be phosphate- or phosphonate-based flame retardant molecules. The phosphorus-based flame retardant molecules can be synthesized as needed, or obtained from a commercial source. The structures and syntheses of phosphorus-based flame retardant molecules are discussed in greater detail with respect to FIGS. 3A-3D.

Process 100 continues with the formation of an itaconic acid derivative. This is illustrated at step 108. The derivatives can have one, two, or three hydroxyl groups to which phosphorus-based flame retardant molecules with allyl or epoxy functional groups can be bound. Examples of itaconic acid derivatives are discussed in greater detail with respect to FIGS. 4A and 4B. It should be noted that the formation of the itaconic derivative in step 108 is illustrated as occurring after the formation of the phosphorus-based flame retardant molecule in step 104. However, in some embodiments, step 108 can occur before step 104. Further, steps 104 and 108 can occur simultaneously in some embodiments.

The itaconic acid derivative and the phosphorus-based flame retardant molecule are chemically reacted in order to form an itaconic acid-based flame retardant compound. This is illustrated at step 112. However, it should be noted that in some embodiments itaconic acid itself is reacted with the phosphorus-based flame retardant molecule instead of an itaconic acid derivative. The identity of the itaconic acid-based flame retardant compound is determined by the itaconic acid derivative and the phosphorus-based flame retardant molecule used in the reaction. The FR groups are bonded to hydroxyl and/or carboxylic acid groups on the itaconic acid derivatives in a reaction with itaconic acid derivatives and the phosphorus-based flame retardant compounds. The syntheses and structures of itaconic acid-based flame retardant compounds are discussed in greater detail with respect to FIGS. 5A-5G and 6A-6D.

The itaconic acid-based flame retardant compound formed in step 112 is polymerized, or added to another polymer, yielding a flame retardant itaconic acid-based polymer. This is illustrated at step 116. The itaconic acid-based flame retardant compounds can be added to a polymer as small molecules, cross-linkers, or bound monofunctional molecules. Further, the flame retardant itaconic acid-based compound can be polymerized in a reaction with a base and/or a second monomer. Additionally, in some embodiments, the flame retardant itaconic acid-based compound can be polymerized in a reaction with a Ziegler-Natta catalyst. Polymerization reactions with the flame retardant itaconic acid-based compounds are discussed in greater detail with respect to FIG. 7B.

Figure 2A:
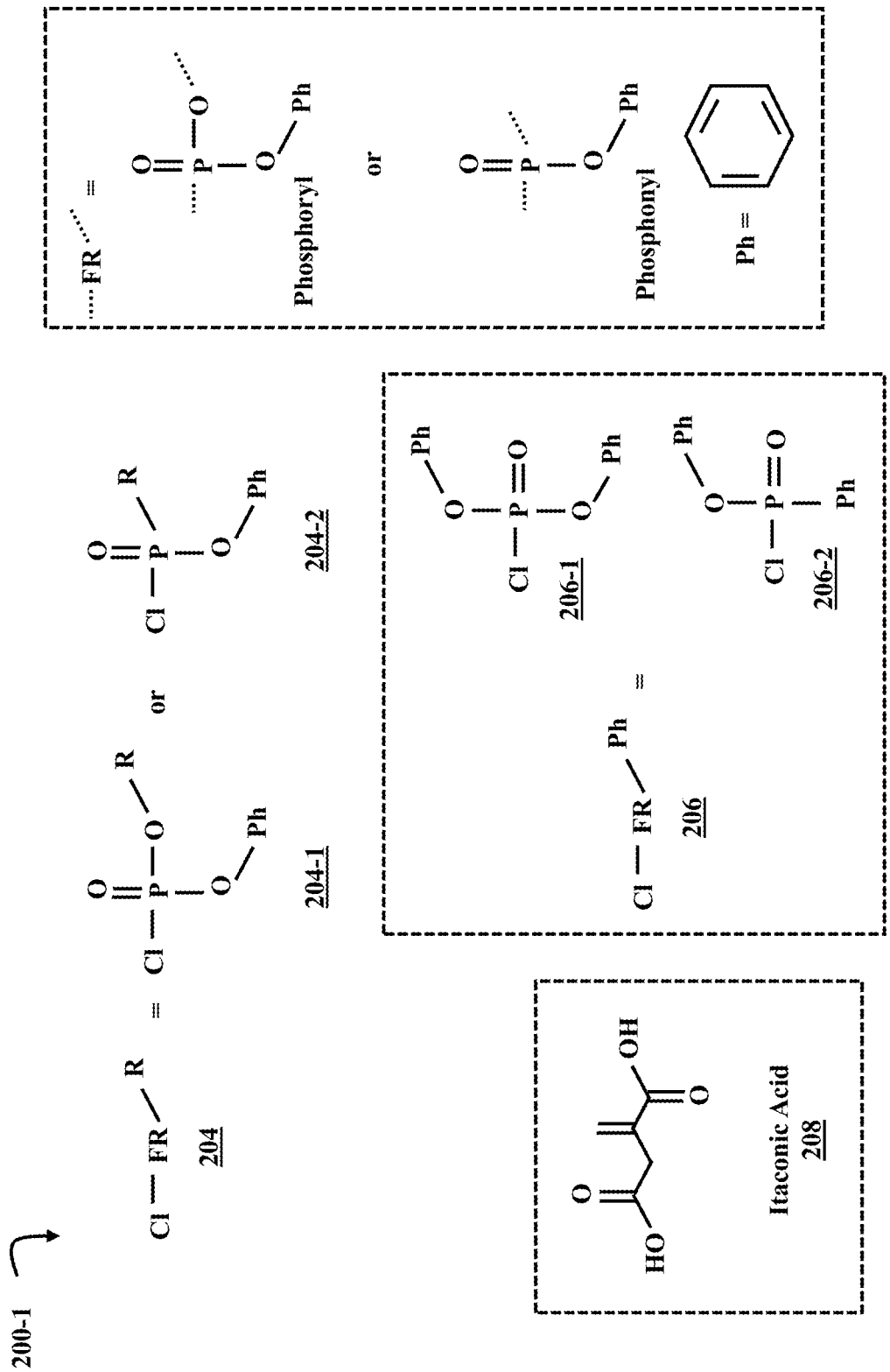
FIG. 2A is a diagrammatic representation of the molecular structures of R-functionalized phosphorus-based flame retardant molecules, phenyl-substituted flame retardant phosphorus-based flame retardant molecules, and itaconic acid, according to some embodiments of the present disclosure.

FIG. 2A is a diagrammatic representation of the molecular structures 200 of R-functionalized phosphorus-based flame retardant molecules 204-1 and 204-2 (referred to collectively as 204), phenyl-substituted phosphorus-based flame retardant molecules 206-1 and 206-2 (referred to collectively as 206), and itaconic acid 208, according to some embodiments of the present disclosure. Each phosphorus-based flame retardant molecule is either a phosphate-based flame retardant molecule 204-1 and 206-1 or phosphonate-based flame retardant molecule 204-2 and 206-2. Herein, phosphoryl and phosphonyl moieties in the phosphate- and phosphonate-based compounds, respectively, are replaced by the abbreviation "FR" in order to simplify illustrations of the molecular structures. The moieties replaced by the abbreviation each have a phenyl substituent. However, this phenyl can be replaced by another alkyl substituent (e.g., methyl, ethyl, propyl, isopropyl, etc.).

The compounds referred to as phenyl-substituted flame retardant phosphorus-based flame retardant molecules 206, each have two phenyl (Ph) substituents. The compounds referred to as R-functionalized phosphorus-based flame retardant molecules 204 each have an R functional group in addition to a single phenyl (Ph) substituent. In some embodiments, the phenyl substituents are replaced by another alkyl substituent (e.g., methyl, ethyl, propyl, isopropyl, etc.). Example syntheses of the R-functionalized phosphorus-based flame retardant molecules 204 are discussed with respect to FIGS. 3A and 3B. The phosphorus-based flame retardant molecules 204 and 206 are reacted with itaconic acid or itaconic acid derivatives to form itaconic acid-based flame retardant compounds.

Herein, itaconic acid-based flame retardant compounds are referred to as functionalized (monofunctionalized, difunctionalized, or trifunctionalized) or phenyl-substituted. Terminal functional groups attached to FR moieties (e.g., allyl, epoxy, and propylene carbonate R groups) are involved in binding to polymer chains or in polymerization reactions, while the phenyl substituents on the FR moieties do not participate in these reactions. Therefore, any compound with at least one functional group is referred to as functionalized to indicate that it will participate in binding or polymerization. Itaconic acid-based flame retardant compounds with only phenyl-substituents on their FR moieties cause a polymer to be flame retardant when blended into the polymer.

Figure 2B:
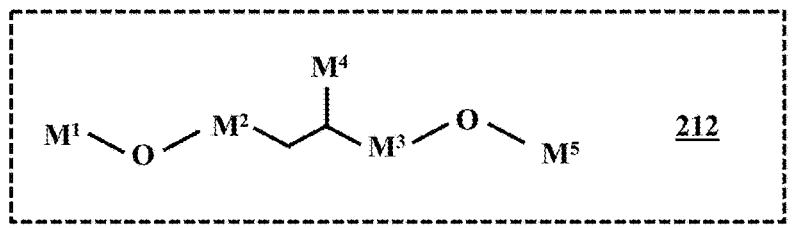
FIG. 2B is a diagrammatic representation of the molecular structure of a generic itaconic acid-based flame retardant compound, according to some embodiments of the present disclosure.
Figure 2B:
Figure 2B:
Figure 2B:
Figure 2B:
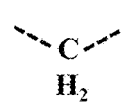
Figure 2B:
Figure 2B:
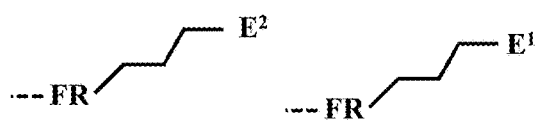
Figure 2B:
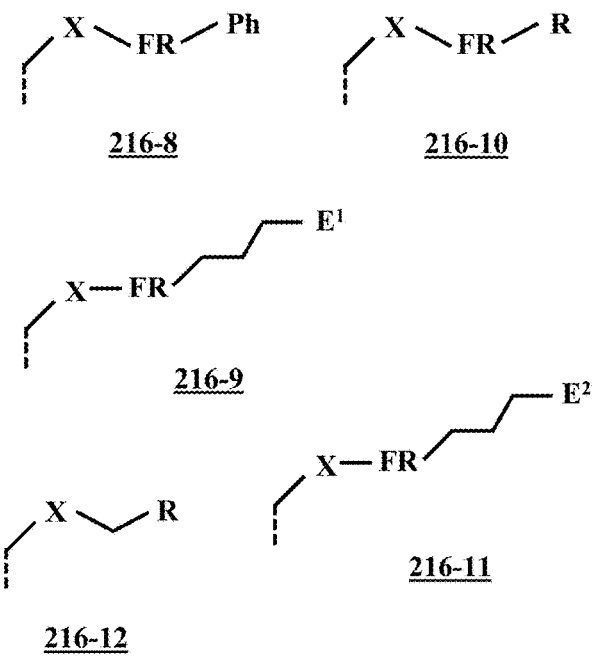

FIG. 2B is a diagrammatic representation 200-2 of the molecular structure of a generic itaconic acid-based flame retardant compound 212, according to some embodiments of the present disclosure. The itaconic acid-based flame retardant compound 212 has several variable positions, which are represented by "M" in the diagram. These positions can have functional groups (e.g., R groups) that will participate in polymerization reactions, or bind to polymers. The positions can also have substituents (e.g., phenyl (Ph) or other alkyl groups) that do not participate in binding or polymerization. When the itaconic acid-based flame retardant compound 212 has a single functional group, it can bind to an active site in a polymer chain, or be polymerized. Further, when the itaconic acid-based flame retardant compound 212 has more than one functional group, it can bind to one or more active sites in a polymer chain, act as a cross-linker, or be polymerized. When the itaconic acid-based flame retardant compound 212 has no functional groups to participate in binding or polymerization, it can be blended with a polymer as a flame retardant small molecule. These properties are discussed in greater detail below.

Additionally, examples of M moieties are illustrated in FIG. 2B. For example, $M^1$ and $M^5$ are R-functionalized flame retardant groups 216-1 or 216-2 or phenyl (Ph)-substituted flame retardant groups 216-3 or 216-4; $M^2$ and $M^3$ are carbonyl groups 216-5 or methylene bridges 216-6; and $M^4$ is a vinyl group 216-7, an ether (X=O)- or thioether (X=S)-linked phenyl-substituted flame retardant group 216-8 or 216-9, an ether- or thioether-linked functionalized flame retardant group 216-10 or 216-11, or an ether- or thioether-linked R functional group. The identities of the R functional groups are discussed in greater detail below.

Figure 6A:
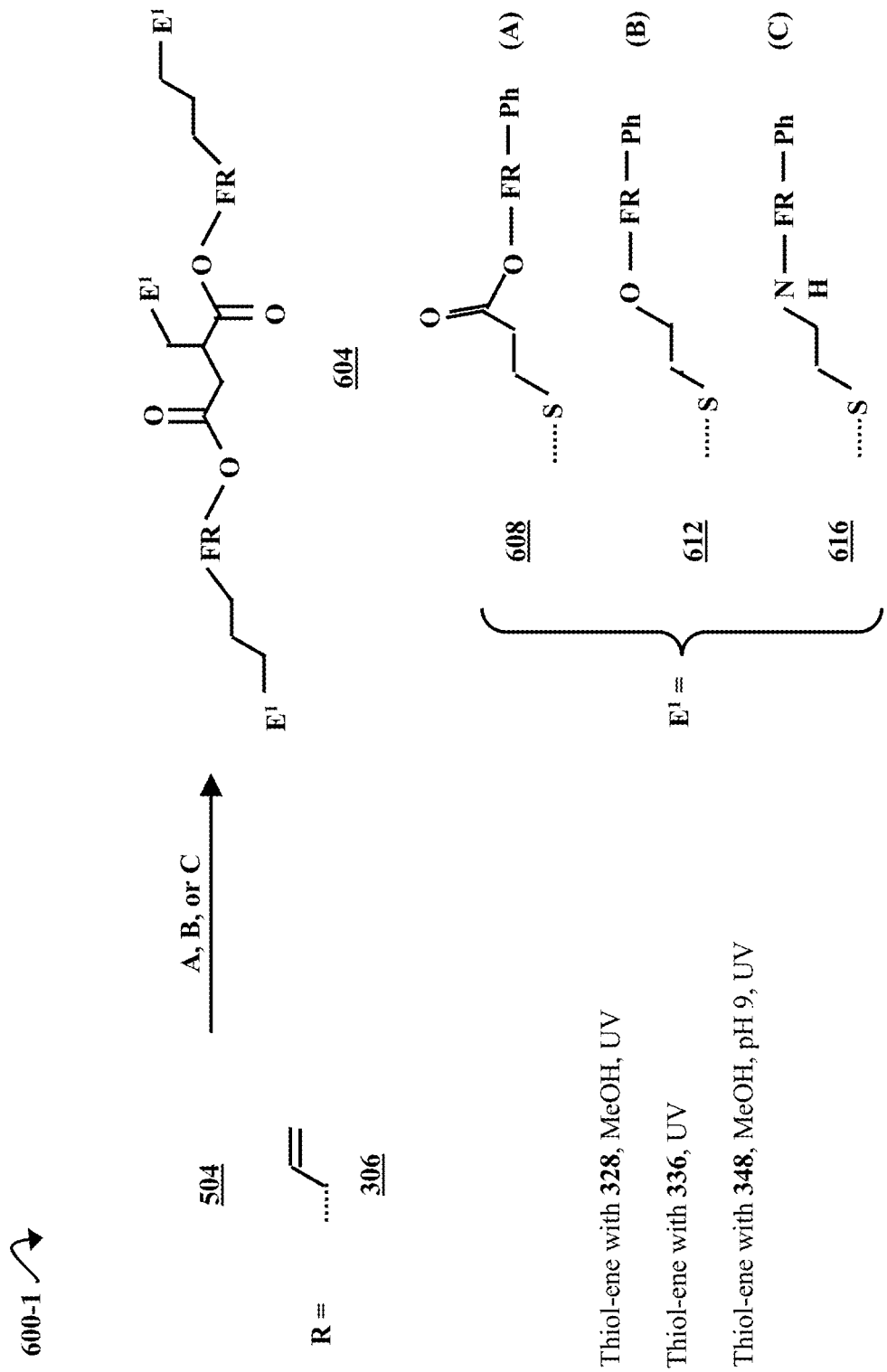
FIG. 6A is a chemical reaction diagram illustrating a process of forming phenyl-substituted thioether-linked flame retardant itaconic acid-based compounds, according to some embodiments of the present disclosure.
Figure 6B:
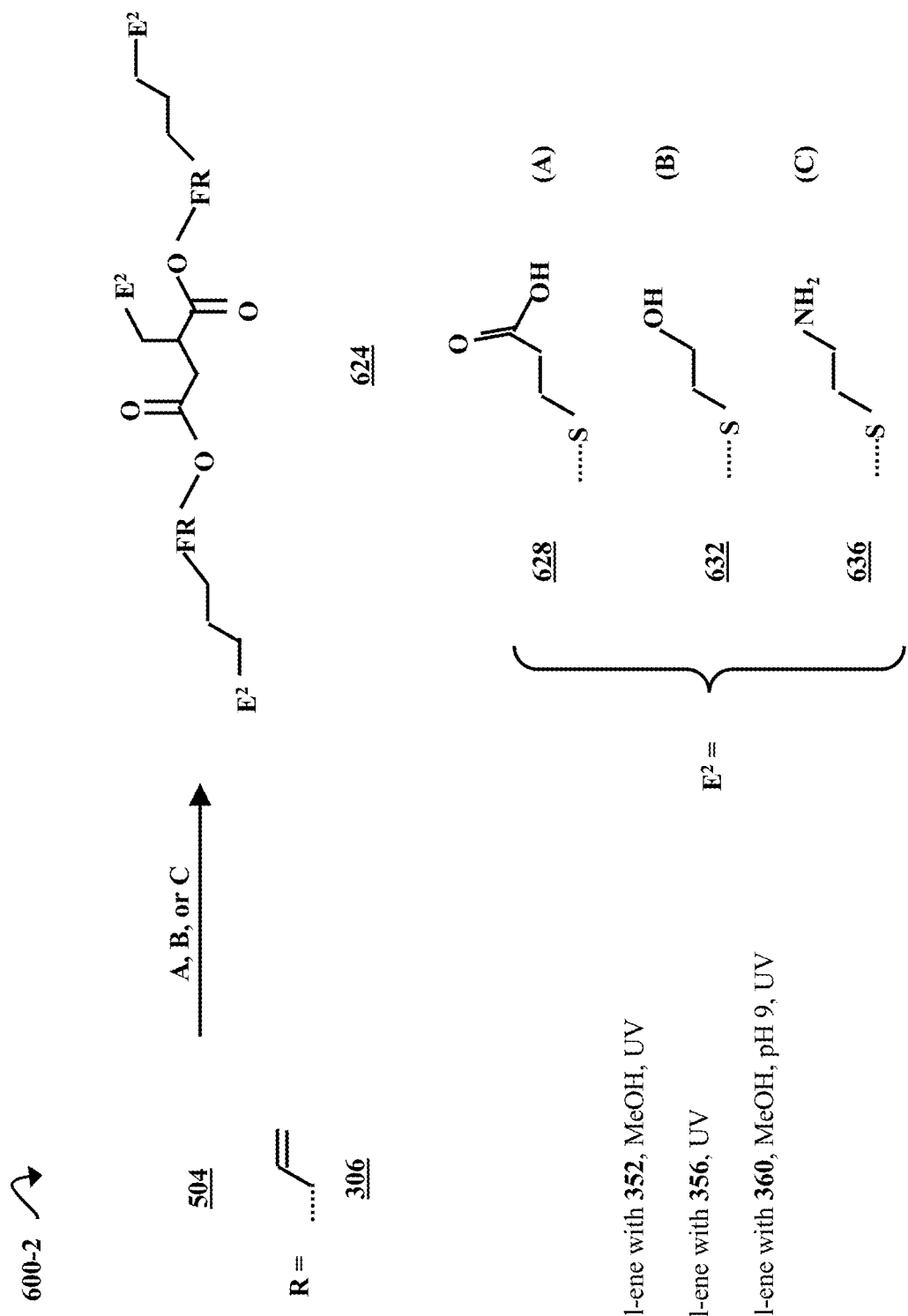
FIG. 6B is a chemical reaction diagram illustrating a process of forming trifunctionalized thioether-linked flame retardant itaconic acid-based compounds, according to some embodiments of the present disclosure.

One of the ether/thioether-linked phenyl-substituted flame retardant groups 216-9 has a phenyl substituent bound to the rest of the group by an additional thioether link. This phenyl-substituted thioether-linked group is referred to herein as $E^1$. Additionally, one of the functionalized ether/thioether-linked flame-retardant groups 216-11 has a functional group bound to the rest of the group by an additional thioether link. This functionalized thioether-linked group is referred to herein as $E^2$. The structures of $E^1$ and $E^2$ are illustrated in FIGS. 6A and 6B, respectively. It should be noted that the flame-retardant groups can be broadly categorized as functionalized (216-1, 216-2, 216-10, and 216-11) or phenyl-substituted (216-3, 216-4, 216-8, and 216-9). The structures of the flame retardant groups and itaconic acid-based flame retardant compounds are discussed in greater detail below.

Figure 3A:
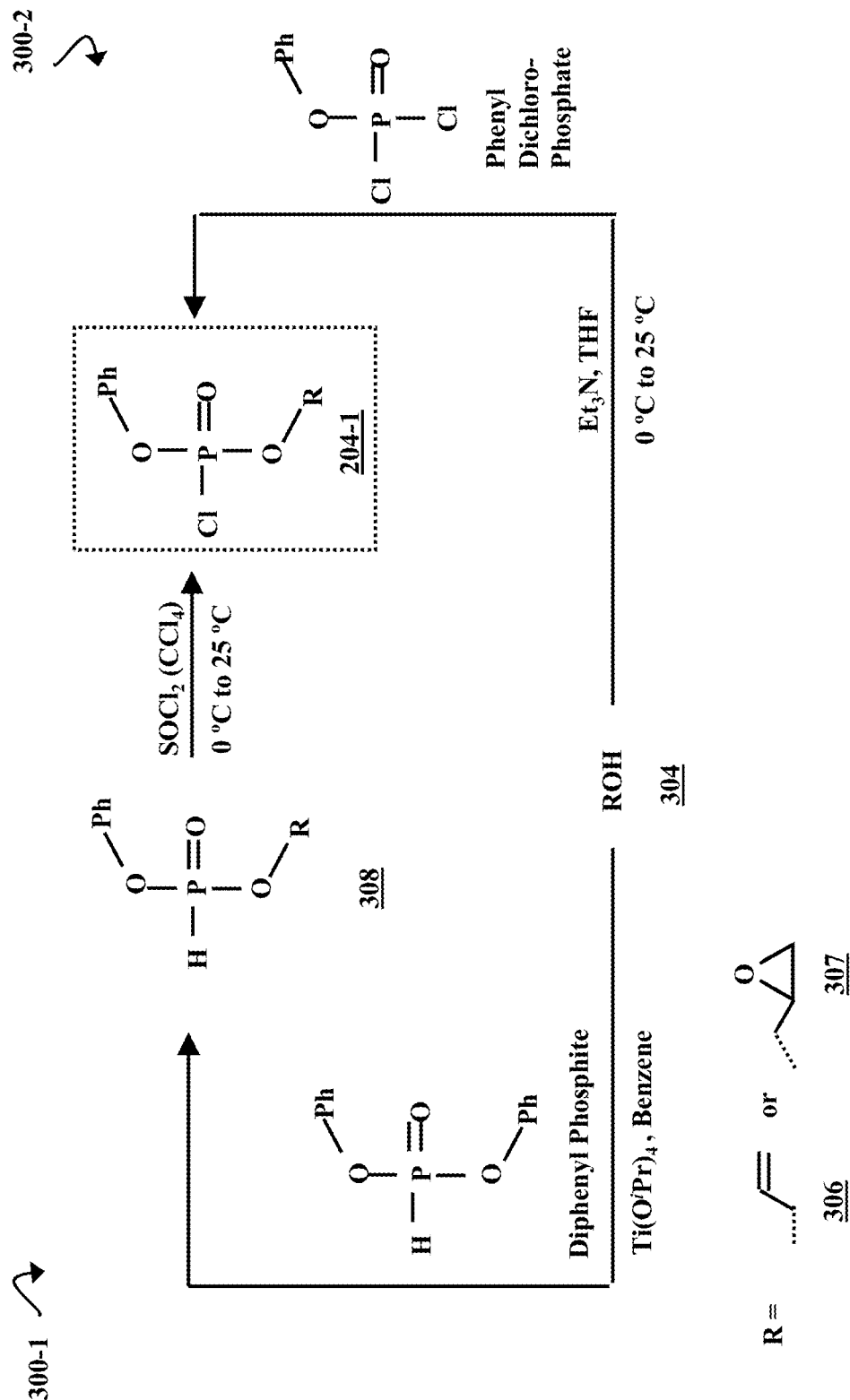
FIG. 3A is a chemical reaction diagram illustrating two processes of synthesizing an R-functionalized phosphate-based flame retardant molecule, according to some embodiments of the present disclosure.

FIG. 3A is a chemical reaction diagram illustrating two processes 300-1 and 300-2 of synthesizing an R-functionalized phosphate-based flame retardant molecule 204-1, according to some embodiments of the present disclosure. In both processes 300-1 and 300-2, an alcohol 304 is a starting material for the R-functionalized phosphate-based flame retardant molecule 204-1. The alcohol 304 has either an allyl R group 306 or an epoxy R group 307. It should be noted that, though an allyl group 306 with a single methylene spacer group is illustrated here, other alcohols with allylic chains of varying lengths (e.g., one to twelve methylene spacer groups) could be used. Additionally, alcohols with acrylate substituents are used in some embodiments.

In process 300-1, the alcohol 304 is reacted with diphenyl phosphite and titanium isopropoxide (Ti(O$^i$Pr)$_4$) in benzene to produce a precursor 308 to the R-functionalized phosphate-based flame retardant molecule 204-1. In this pseudo-transesterification reaction, the precursor 308 is formed when a phenyl (Ph) substituent on diphenyl phosphite is replaced by the R group from the alcohol 304. The precursor 308 is then reacted with thionyl chloride ($SOCl_2$) and carbon tetrachloride ($CCl_4$) over a range of approximately 0° C. to room temperature (RT, e.g., 15-25° C.), forming the R-functionalized phosphate-based flame retardant molecule 204-1. In process 300-2, the alcohol 304 is reacted with phenyl dichlorophosphate in a tetrahydrofuran (THF) solution containing triethylamine ($Et_3N$). This process is carried out over a range of approximately 0° C. to room temperature (RT, e.g., 15-25° C.). A chloride on the phenyl dichlorophosphate is replaced by the alcohol 304, forming the R-functionalized phosphate-based flame retardant molecule 204-1.

Figure 3B:
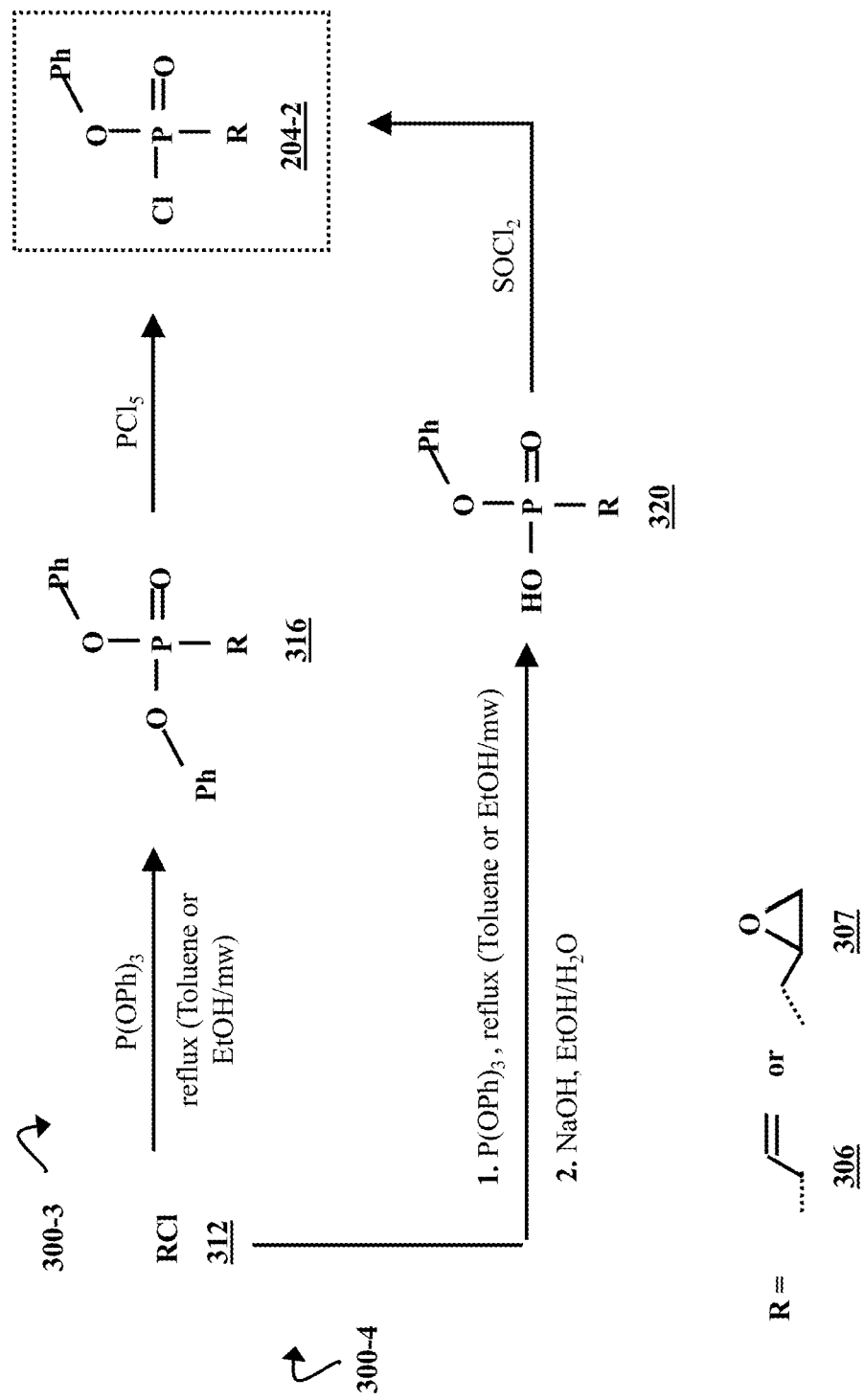
FIG. 3B is a chemical reaction diagram illustrating two processes of synthesizing an R-functionalized phosphonate-based flame retardant molecule, according to some embodiments of the present disclosure.

FIG. 3B is a chemical reaction diagram illustrating two processes 300-3 and 300-4 of synthesizing an R-functionalized phosphonate-based flame retardant molecule 204-2, according to some embodiments of the present disclosure. In both processes 300-3 and 300-4, an organochloride 312 is a starting material for the R-functionalized phosphonate-based flame retardant molecule 204-2. The organochloride has either an allyl R group 306 or an epoxy R group 307. It should be noted that, as in the case of the alcohol 304, other organochlorides with allylic chains of varying lengths (e.g., one to twelve methylene spacer groups) could be used. Additionally, organochlorides with acrylate substituents are used in some embodiments.

In process 300-3, the organochloride 312 is reacted with triphenyl phosphite ($P(OPh)_3$). The mixture is heated, either by refluxing in toluene or microwaving (mw) in ethanol (EtOH), producing a phosphonyl ester precursor 316 to the R-functionalized phosphonate-based flame retardant molecule 204-2. The phosphonyl ester precursor 316 is reacted with phosphorus pentachloride ($PCl_5$) to form the R-functionalized phosphonate-based flame retardant molecule 204-2.

In process 300-4, a mixture of the organochloride 312 and triphenyl phosphite ($P(OPh)_3$) is heated, either by refluxing in toluene or microwaving (mw) in ethanol (EtOH), forming a phenylphosphinic acid precursor 320 to the R-functionalized phosphonate-based flame retardant molecule 204-2. The reaction is then quenched by raising the pH of the solution. In this example, an ethanol (EtOH)/water ($H_2O$) solution of sodium hydroxide (NaOH) is added to the reaction mixture. However, in some embodiments, bases other than sodium hydroxide, such as potassium hydroxide or lithium hydroxide, are used to quench the reaction. When the reaction has been quenched, thionyl chloride ($SOCl_2$) is added to the phenylphosphinic acid precursor 320, producing the R-functionalized phosphonate-based flame retardant molecule 204-2.

Figure 3C:
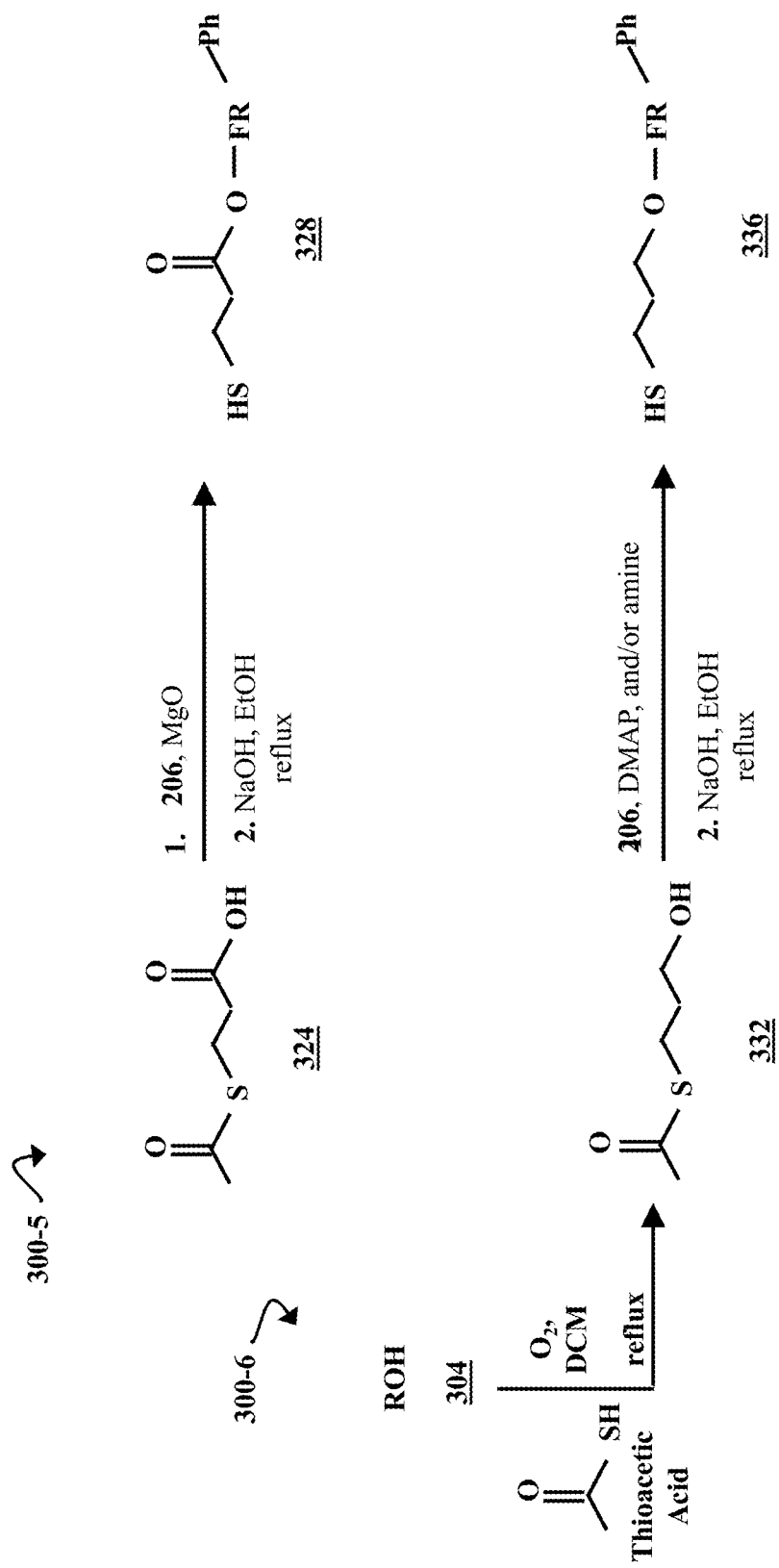
FIG. 3C is a chemical reaction diagram illustrating a process of synthesizing a carboxylic acid-derived flame retardant thiol molecule and a process of synthesizing a hydroxy-derived flame retardant thiol molecule, according to some embodiments of the present disclosure.

FIG. 3C is a chemical reaction diagram illustrating a process 300-5 of synthesizing a carboxylic acid-derived flame retardant thiol molecule 328 and a process 300-6 of synthesizing a hydroxy-derived flame retardant thiol molecule 336, according to some embodiments of the present disclosure. In process 300-5, acetate-protected thiopropionic acid 324 is reacted with magnesium oxide (MgO) and a phenyl-substituted phosphorus-based flame retardant compound 206. The acetate group is then removed by refluxing the mixture in an ethanol (EtOH) solution containing sodium hydroxide (NaOH), yielding the carboxylic acid-derived flame retardant thiol molecule 328. If the process is carried out with 206-1, the carboxylic acid-derived flame retardant thiol molecule 328 will have phosphoryl FR groups, and, if the reaction is carried out with 206-2, the carboxylic acid-derived flame retardant thiol molecule 328 will have phosphonyl FR groups.

In process 300-6, the alcohol 304 with the allyl R group 306 is reacted with thioacetic acid in a thiol-ene reaction. In the first step of the reaction, oxygen ($O_2$) is added to a dichloromethane (DCM) solution of the allyl alcohol 304 and thioacetic acid. The mixture is refluxed, resulting in an acetate-protected mercaptopropanol 332. The second step in the reaction is a substitution reaction involving a phenyl-substituted phosphorus-based flame retardant compound 206, catalytic dimethylaminopyridine (cat. DMAP), and/or a stoichiometric amount of an organic amine, such as triethylamine. The acetate group is removed by refluxing the mixture in an ethanol (EtOH) solution containing sodium hydroxide (NaOH). This step results in the production of the hydroxy-derived flame retardant thiol molecule 336. If the process is carried out with 206-1, the hydroxy-derived flame retardant thiol molecule 336 will have phosphoryl FR groups, and, if the reaction is carried out with 206-2, the hydroxy-derived flame retardant thiol molecule 336 will have phosphonyl FR groups.

Figure 3D:
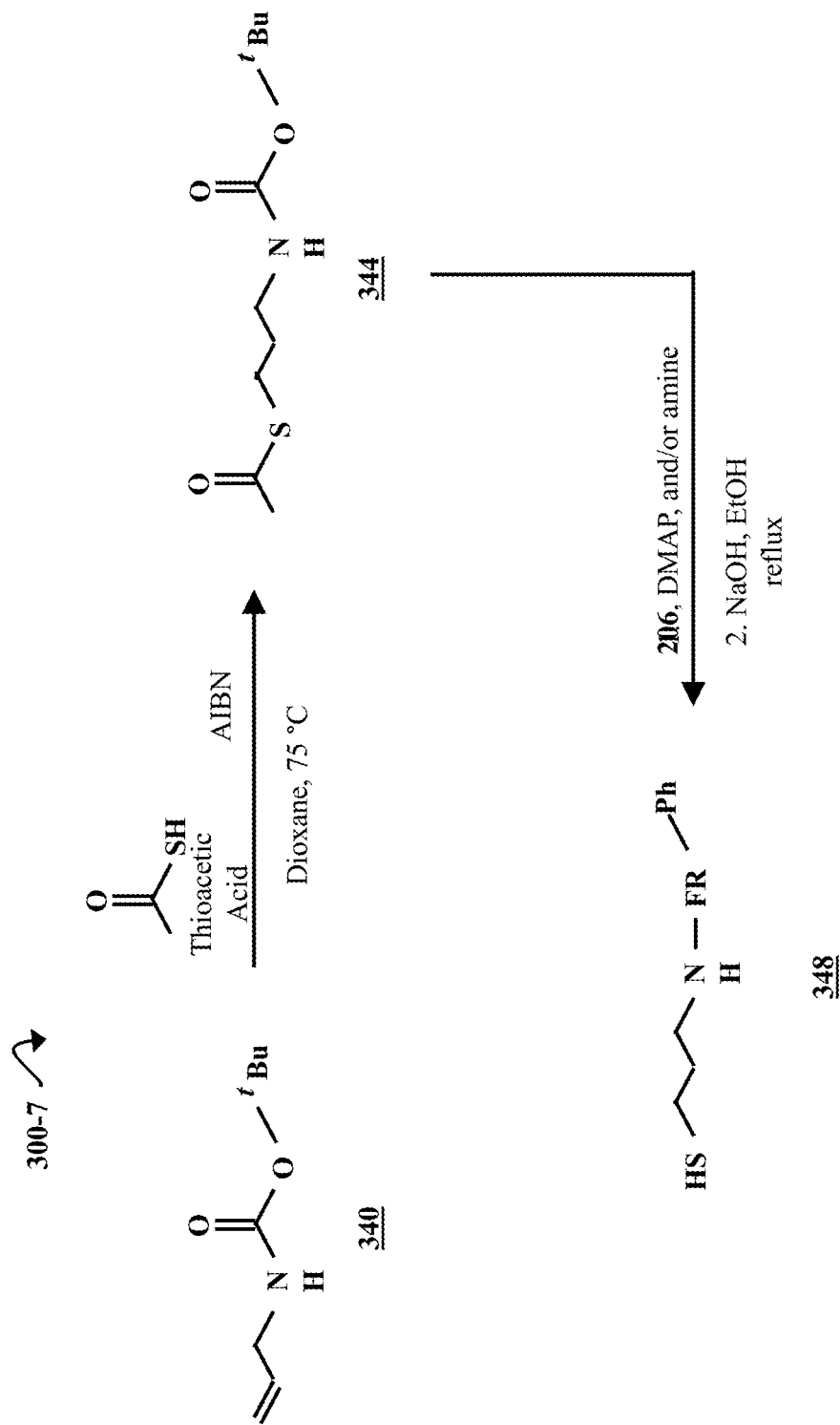
FIG. 3D is a chemical reaction diagram illustrating a process of synthesizing an amine-derived flame retardant thiol molecule, according to some embodiments of the present disclosure.

FIG. 3D is a chemical reaction diagram illustrating a process 300-7 of synthesizing an amine-derived flame retardant thiol molecule 348, according to some embodiments of the present disclosure. In process 300-7, 1-(boc-amino)-3-butene 340 is first reacted with thioacetic acid in a thiol-ene reaction. Azobisisobutyronitrile (AIBN) is added to the dioxane solution of 1-(boc-amino)-3-butene 340 and thioacetic acid, and the mixture is stirred at 75° C., resulting in an acetate-protected precursor 344 to the amine-derived flame retardant thiol molecule 348. The second step in process 300-7 is a substitution reaction with a phenyl-substituted phosphorus-based flame retardant compound 206, catalytic dimethylaminopyridine (cat. DMAP), and/or a stoichiometric amount of an organic amine, such as triethylamine. The acetate group and boc groups are removed under basic conditions (e.g., by refluxing the mixture in an ethanol (EtOH) solution containing sodium hydroxide (NaOH)). This step results in the production of the amine-derived flame retardant thiol molecule 348. If the process is carried out with 206-1, the amine-derived flame retardant thiol molecule 348 will have phosphoryl FR groups, and, if the reaction is carried out with 206-2, the amine-derived flame retardant thiol molecule 348 will have phosphonyl FR groups.

Figure 3E:
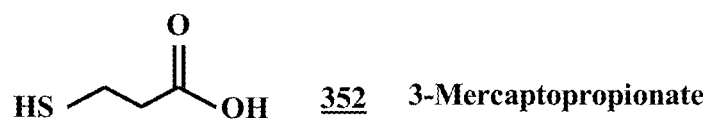
FIG. 3E is a diagrammatic representation of the molecular structures of three thiol molecules that are involved in the synthesis of itaconic acid-based compounds, according to some embodiments of the present disclosure.
Figure 3E:
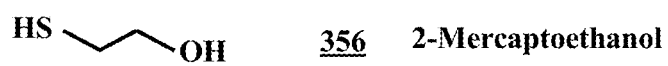
Figure 3E:
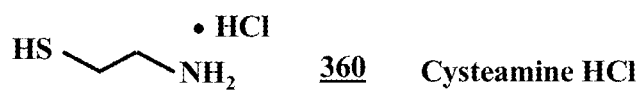

FIG. 3E is a diagrammatic representation of the molecular structures 302 of three thiol molecules that are involved in the synthesis of the itaconic acid-based compounds, according to some embodiments of the present disclosure. The three thiol molecules are 3-mercaptopropionate 352, 2-mercaptoethanol 356, and cysteamine hydrochloride (HCl) 360. Each of these thiols can provide a thioether with a functional group in the synthesis of a functionalized thioether-linked flame retardant itaconic acid-based compound. The syntheses and structures of the functionalized thioether-linked flame retardant itaconic acid-derived cross-linkers are discussed in greater detail with respect to FIGS. 6B and 6D.

Figure 4A:
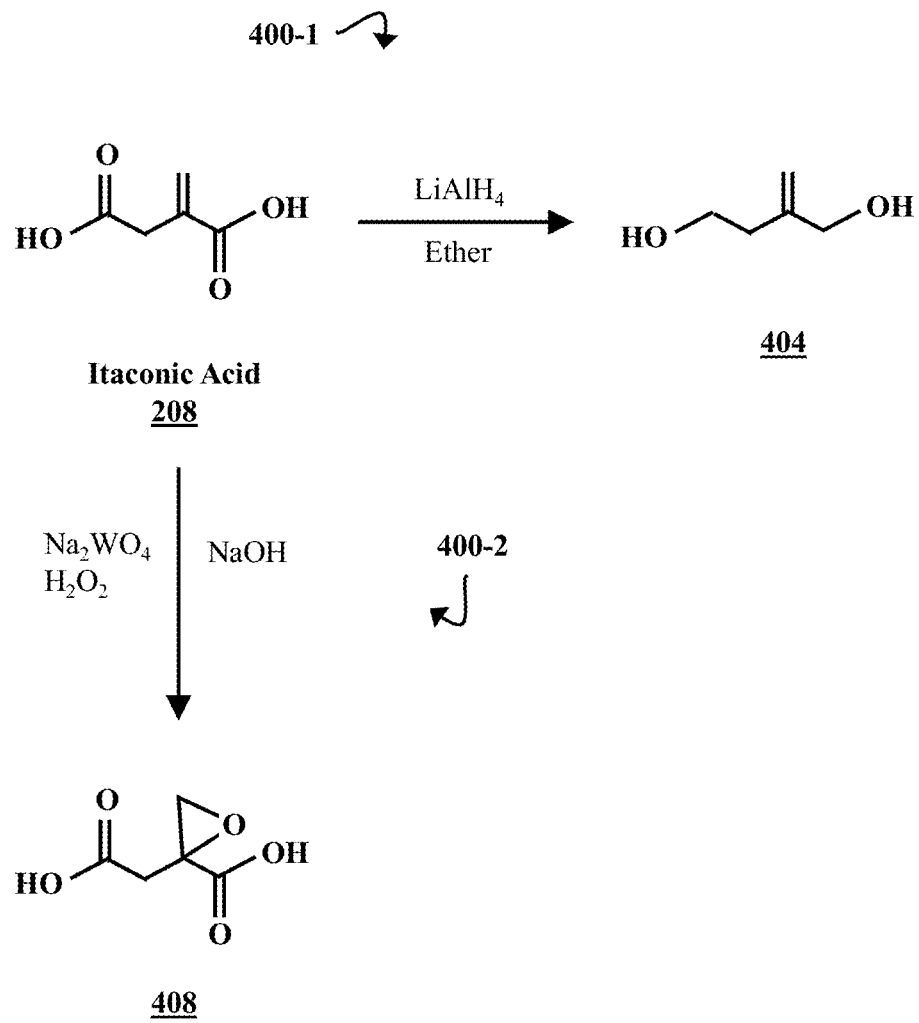
FIG. 4A is chemical reaction diagram illustrating processes of synthesizing itaconic acid-derived 2-methylenebutane-1,4-diol and 2-carboxy-oxiranylacetic acid, according to some embodiments of the present disclosure.

FIG. 4A is chemical reaction diagram illustrating processes 400-1 and 400-2 of synthesizing itaconic acid-derived 2-methylenebutane-1,4-diol 404 and 2-carboxy-oxiranylacetic acid 408, according to some embodiments of the present disclosure. In process 400-1, itaconic acid 208 is reduced by lithium aluminum hydride ($LiAlH_4$) in ether. This reduction reaction produces the 2-methylenebutane-1,4-diol 404. However, it should be noted that, under the appropriate reaction conditions, process 400-1 can use reducing agents other than LiAlH$_4$ (e.g., H$_2$ with Pd/C, sodium borohydride (NaBH$_4$) and an electrophile (e.g., iodine), carbon monoxide (CO), iron(II) compounds, etc.). In process 400-2, itaconic acid 208 is reacted with hydrogen peroxide (H$_2$O$_2$) and sodium tungstate (Na$_2$WO$_4$) in an aqueous solution of sodium hydroxide (NaOH). This reaction produces an epoxide at the itaconic acid 208 vinyl group, forming the 2-carboxy-oxiranylacetic acid 408.

Figure 4B:
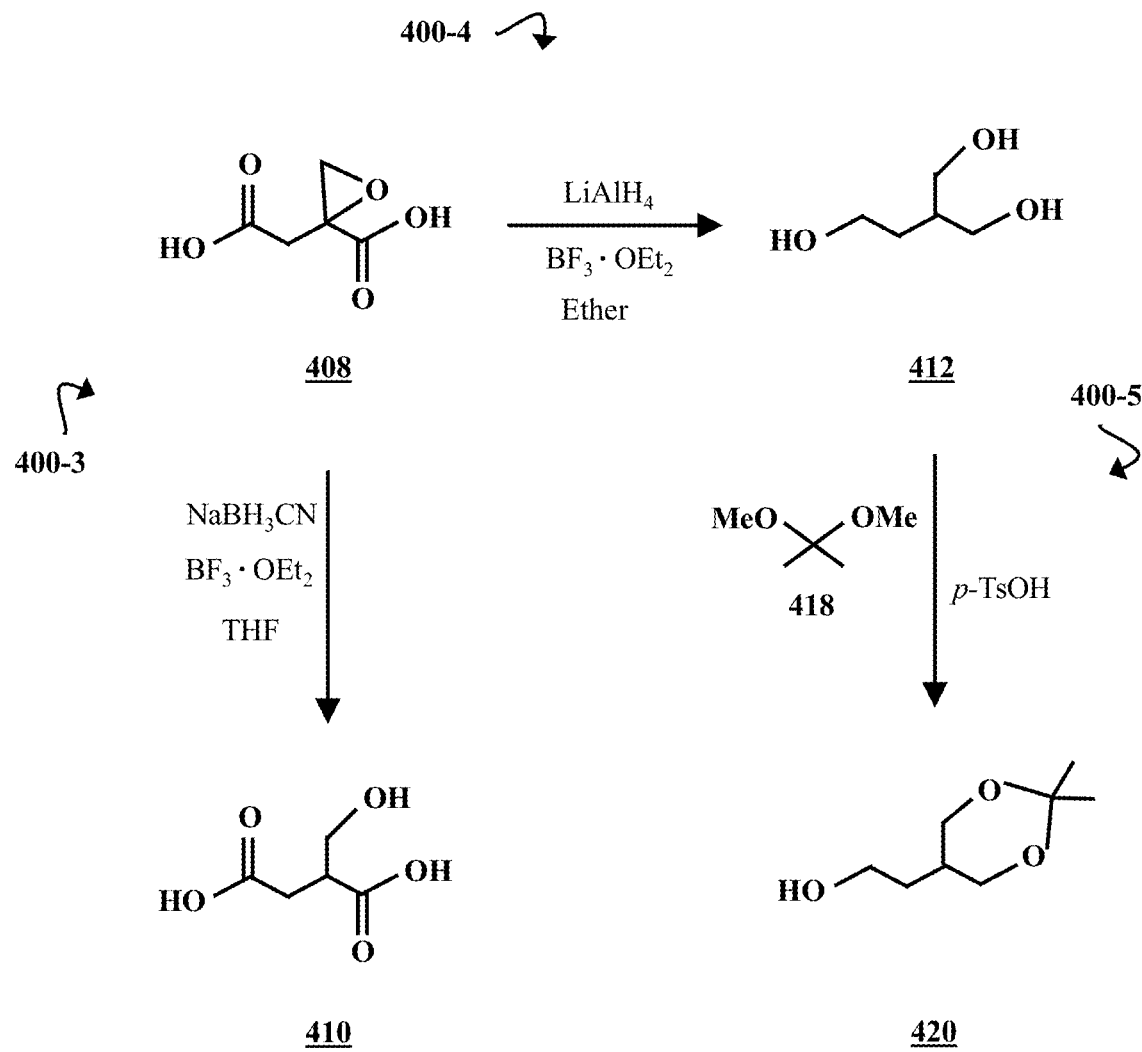
FIG. 4B is a chemical reaction diagram illustrating processes of synthesizing 2-carboxy-oxiranylacetic acid-derived 2-(hydroxymethyl)butane-1,4-diol, 2-(hydroxymethyl)succinic acid, and 2-(2,2-dimethyl-1,3-dioxan-5-yl)ethanol, according to some embodiments of the present disclosure.

FIG. 4B is a chemical reaction diagram illustrating processes 400-3, 400-4, and 400-5 of forming 2-carboxy-oxiranylacetic acid-derived 2-(hydroxymethyl)succinic acid 410, 2-(hydroxymethyl)butane-1,4-diol 412, and 2-(2,2-dimethyl-1,3-dioxan-5-yl)ethanol 420, according to some embodiments of the present disclosure. In process 400-3, a ring-opening reaction between the 2-carboxy-oxiranylacetic acid 408 derived from itaconic acid in process 400-2, sodium cyanborohydride (NaBH$_3$CN), and boron trifluoride etherate (BF$_3$·Et$_2$O) in tetrahydrofuran (THF) produces 2-(hydroxymethyl)succinic acid 410. In process 400-4, a ring-opening reaction is carried out on the 2-carboxy-oxiranylacetic acid 408 by reacting it with boron trifluoride diethyl etherate (BF$_3$·Et$_2$O) in an ether solution. A simultaneous reduction by LiAlH$_4$ produces the 2-(hydroxymethyl)butane-1,4-diol 412. In process 400-5, the 2-(hydroxymethyl)butane-1,4-diol 412 is reacted with 2,2-dimethoxypropane 418 and p-toluenesulfonic acid to produce 2-(2,2-dimethyl-1,3-dioxan-5-yl)ethanol 420.

Figure 5A:
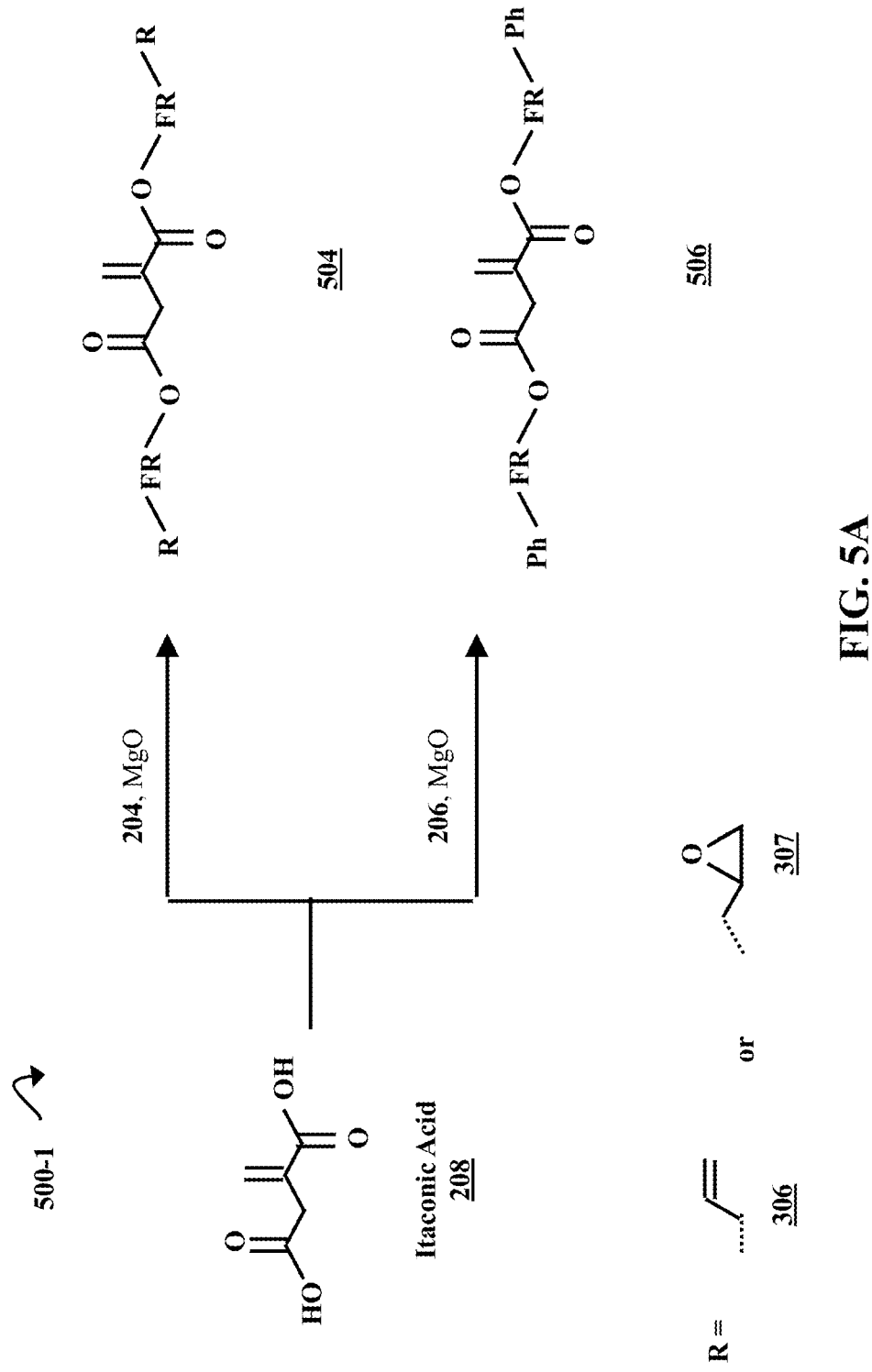
FIG. 5A is a chemical reaction diagram illustrating a process of forming a difunctionalized itaconic acid-based flame retardant compound and a phenyl-substituted itaconic acid-based flame retardant compound, according to some embodiments of the present disclosure.

FIG. 5A is a chemical reaction diagram illustrating a process 500-1 of forming a difunctionalized itaconic acid-based flame retardant compound 504 and a phenyl-substituted itaconic acid-based flame retardant compound 506, according to some embodiments of the present disclosure. In both reactions, itaconic acid 208 is reacted with a phosphorus-based flame-retardant molecule 204 or 206 and magnesium oxide (MgO). When the reaction is carried out with an R-functionalized phosphorus-based compound 204, allyl-306 or epoxy- 307 functionalized FR moieties are attached at the carboxylic acid groups on itaconic acid 208. This reaction forms a difunctionalized itaconic acid-based flame retardant compound 504. This compound 504 is a flame retardant itaconic acid-based compound that can be polymerized, or act as a cross-linker in another polymer. Its inclusion in a polymer, either by polymerization or cross-linking, causes the polymer to be flame retardant.

If the reaction 500-1 is carried out with a phenyl-substituted phosphorus based compound 206, phenyl-substituted FR moieties are attached at the carboxylic acid groups, and the phenyl-substituted itaconic acid-based flame retardant compound 506 is formed. This compound 506 is a flame retardant itaconic acid-based small molecule, which can be blended with a polymer to add flame retardancy to the polymer. It should be noted that reactions with phosphorus-based flame retardant molecules 204 and/or 206 and MgO can attach FR moieties to carboxylic acid groups on any of the itaconic acid-based compounds disclosed herein that have carboxylic acid groups (e.g., compounds 408 and 410). Further, it should be noted that an epoxy R group can be produced by reacting an allyl functional group 306 with a peroxide reagent, such as meta-chloroperoxybenzoic acid (mCPBA). Further, epoxy R groups 307 can ring open in reactions involving nucleophiles.

Figure 5B:
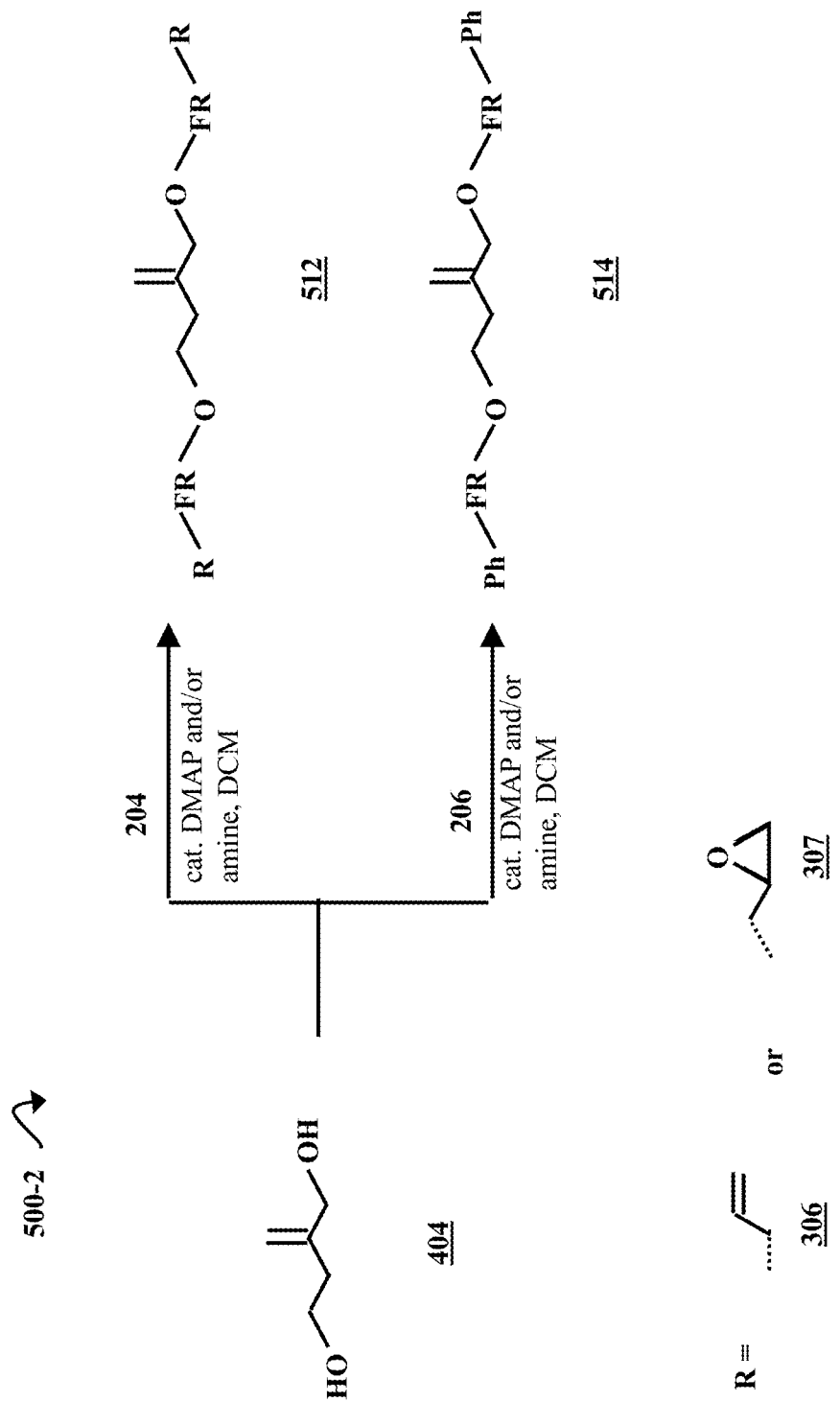
FIG. 5B is a chemical reaction diagram illustrating a process of forming a difunctionalized 2-methylenebutane-1,4-diol-derived flame retardant compound and a phenyl-substituted 2-methylenebutane-1,4-diol-derived flame retardant compound, according to some embodiments of the present disclosure.

FIG. 5B is a chemical reaction diagram illustrating a process 500-2 of forming a difunctionalized 2-methylenebutane-1,4-diol-derived flame retardant compound 512 and a phenyl-substituted 2-methylenebutane-1,4-diol-derived flame retardant compound 514, according to some embodiments of the present disclosure. In both reactions, 2-methylenebutane-1,4-diol 404 is reacted with a phosphorus-based flame-retardant molecule 204 or 206, catalytic dimethylaminopyridine (cat. DMAP), and/or a stoichiometric amount of an organic amine (e.g., triethylamine) in a dichloromethane (DCM) solution. When the reaction is carried out with an R-functionalized phosphorus-based compound 204, allyl-306 or epoxy- 307 functionalized FR moieties are attached at the hydroxyl groups on 2-methylenebutane-1,4-diol 404. This reaction forms the difunctionalized 2-methylenebutane-1,4-diol-derived flame retardant compound 512. Like compound 504, this compound 512 is a flame retardant itaconic acid-based compound that can be polymerized or act as a cross-linker in another polymer. Its inclusion in a polymer, either by polymerization or cross-linking, causes the polymer to be flame retardant.

If the reaction 500-2 is carried out with a phenyl-substituted phosphorus-based compound 206, phenyl-substituted FR moieties are attached at the hydroxyl groups, and the phenyl-substituted 2-methylenebutane-1,4-diol-derived flame retardant compound 514 is formed. Like compound 506, this compound 514 is a flame retardant itaconic acid-based small molecule, which can be blended with a polymer to impart flame retardancy. It should be noted that reactions with a phosphorus-based compound 204 and/or 206, cat. DMAP in DCM, and/or a stoichiometric amount of an organic amine can attach FR moieties to hydroxyl groups that are not part of a carboxylic acid moiety on any of the compounds disclosed herein that have these hydroxyl groups (e.g., compounds 410 and 412).

Figure 5C:
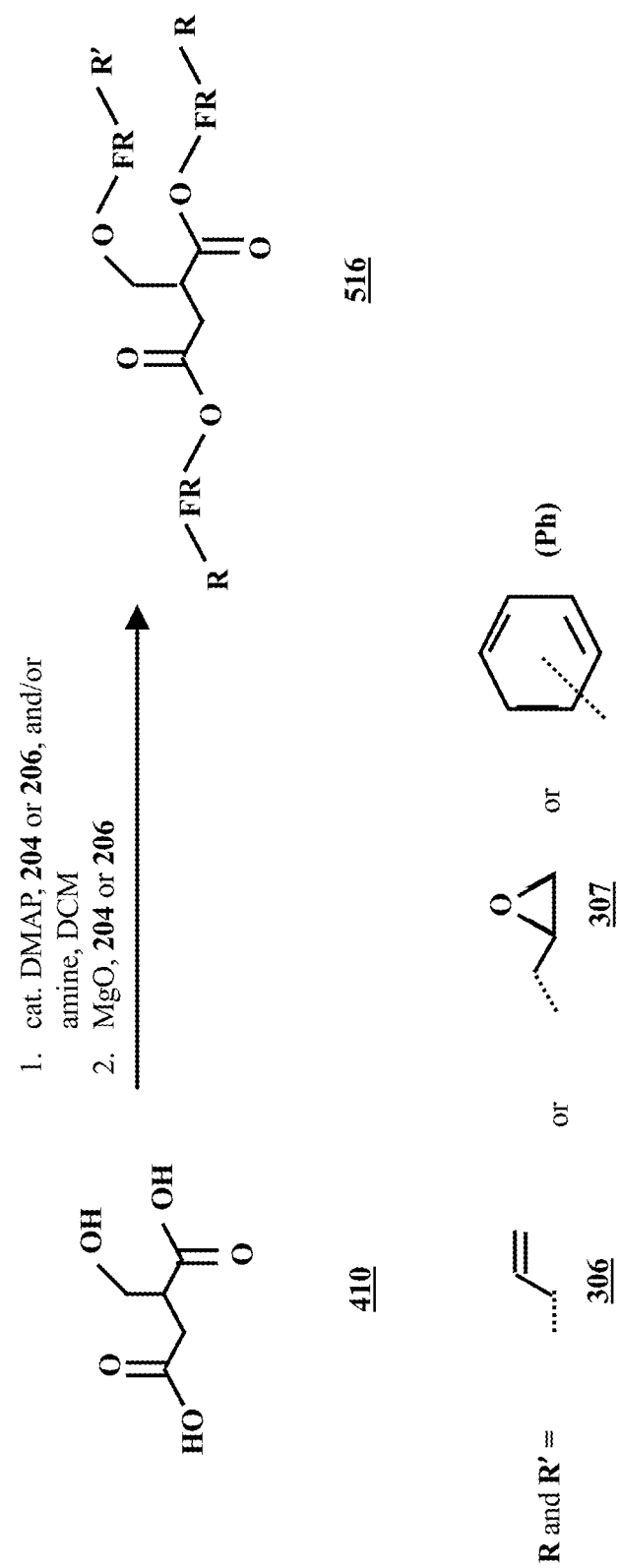
FIG. 5C is a chemical reaction diagram illustrating a process of forming R-functionalized and/or phenyl-substituted 2-(hydroxymethyl)succinic acid-derived flame retardant compounds, according to some embodiments of the present disclosure.

FIG. 5C is a chemical reaction diagram illustrating a process 500-3 of forming R-functionalized and/or phenyl-substituted 2-(hydroxymethyl)succinic acid-derived flame retardant compounds 516, according to some embodiments of the present disclosure. In this reaction, 2-(hydroxymethyl)succinic acid 410 is reacted with a phosphorus-based flame-retardant molecule 204 or 206 in two steps. Carrying out the reaction in multiple steps with different phosphorus-based flame-retardant molecules 204 or 206 allows the formation of monofunctionalized, difunctionalized, trifunctionalized, or phenyl-substituted 2-(hydroxymethyl)succinic acid-derived flame retardant compounds 516. In the first step, an FR moiety with a functional group or phenyl (Ph) substituent represented by R' is added at the location of the hydroxyl group, and in the second step, FR moieties with functional groups or phenyl (Ph) substituents represented by R are added at the location of the carboxylic acid groups.

In the first step, the selected phosphorus-based flame-retardant molecule 204 or 206 is reacted with 2-(hydroxymethyl)succinic acid 410, catalytic dimethylaminopyridine (cat. DMAP) and/or a stoichiometric amount of an organic amine (e.g., triethylamine) in a dichloromethane (DCM) solution. These reaction conditions cause the phosphorus-based flame retardant molecule 204 or 206 to react with the hydroxyl group on 2-(hydroxymethyl)succinic acid 410, and attach an FR moiety. In the second step, the selected phosphorus-based flame-retardant molecule 204 or 206 is reacted with 2-(hydroxymethyl)succinic acid 410 and magnesium oxide (MgO). These reaction conditions cause the phosphorus-based flame retardant molecule 204 or 206 to react with the carboxylic acid group on 2-(hydroxymethyl)succinic acid 410, and attach an FR moiety. Carrying out the syntheses of the 2-(hydroxymethyl)succinic acid-derived flame retardant compounds 516 in multiple steps allows the identity of the R and R' groups and the degree of functionality to be varied.

For example, if steps one and two are both carried out with a phenyl-substituted phosphorus-based flame retardant molecule 206, compound 516 will be a phenyl-substituted flame retardant small molecule that can be blended with materials such as polymers to impart flame retardancy. Further, if steps one and two are both carried out with an R-functionalized flame-retardant phosphorus-based compound 204, compound 516 will be a trifunctionalized flame retardant compound that can be a cross-linker in a polymer, or it can be polymerized to form a flame retardant polymer. The functional R or R' groups on the phosphorus-based compound 204 can be varied between steps one and two, yielding a trifunctionalized compound with different types of functional groups (e.g., two allyl R groups 306 and one epoxy R' group 307).

In some embodiments, varying the R and R' groups on the 2-(hydroxymethyl)succinic acid-derived flame retardant compound 516 can result in compounds with different degrees of functionality. For example, if step one is carried out with a phenyl-substituted phosphorus-based flame retardant molecule 206, and step two is carried out with an R-functionalized phosphorus-based flame retardant molecule 204, compound 516 will be a difunctionalized flame retardant compound where the R groups are each an allyl 306 or epoxy 307 functional group (depending on the choice of R group on compound 204), and where the R' group is a phenyl substituent Like a trifunctionalized compound 516, a difunctionalized flame retardant compound 516 can be a cross-linker, or it can be polymerized. Further, carrying out step one with an R-functionalized phosphorus-based flame retardant molecule 204, and step two with a phenyl-substituted phosphorus-based flame retardant molecule 206, yields a monofunctionalized flame retardant compound 516. Monofunctionalized flame retardant compounds 516 can be polymerized, or bound to polymer chains, causing the polymer to be flame retardant.

Figure 5D:
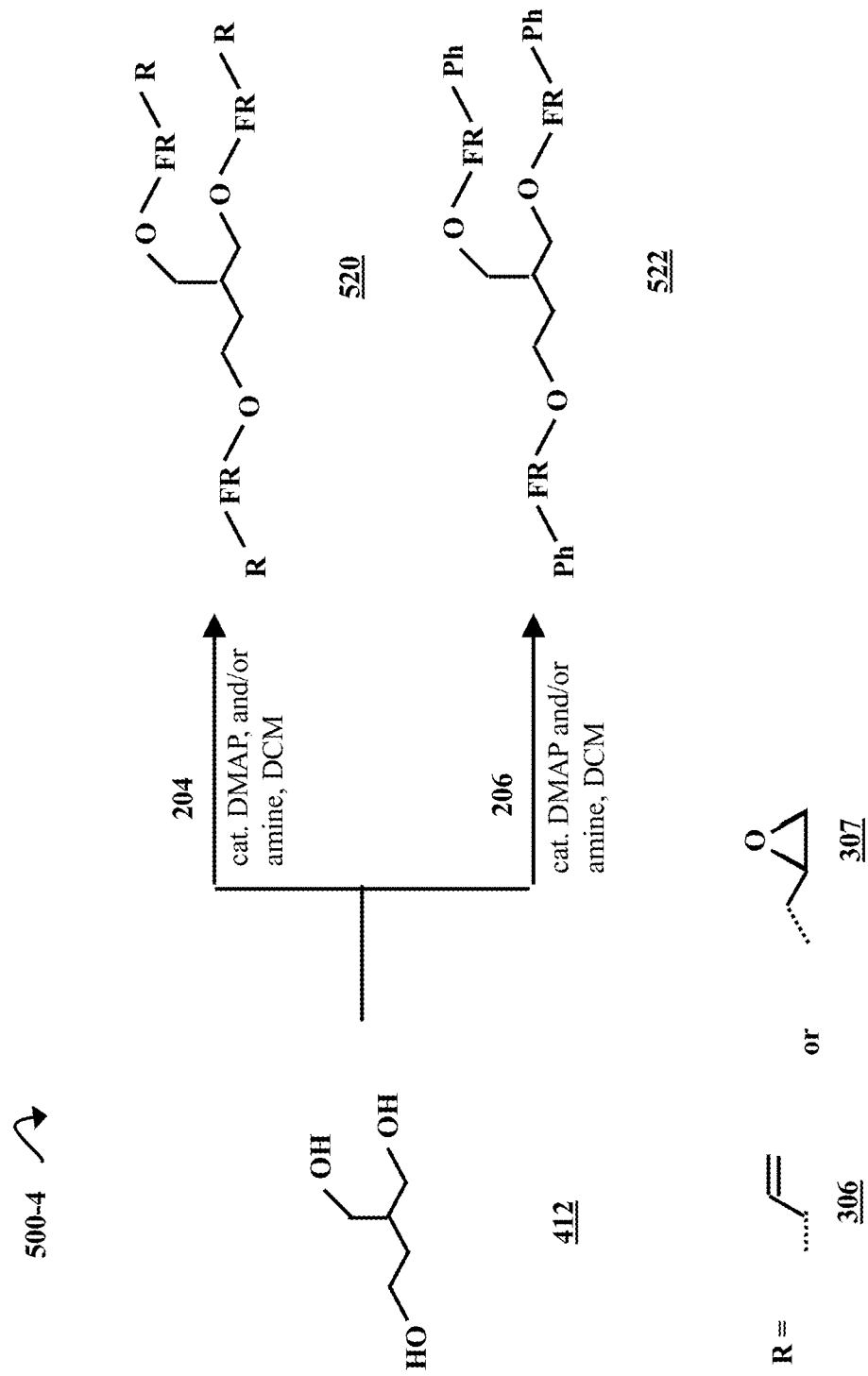
FIG. 5D is a chemical reaction diagram illustrating a process of forming a trifunctionalized 2-(hydroxymethyl)butane-1,4-diol-derived flame retardant compound and a phenyl-substituted 2-(hydroxymethyl)butane-1,4-diol-derived flame retardant compound, according to some embodiments of the present disclosure.

FIG. 5D is a chemical reaction diagram illustrating a process 500-4 of forming a trifunctionalized 2-(hydroxymethyl)butane-1,4-diol-derived flame retardant compound 520 and a phenyl-substituted 2-(hydroxymethyl)butane-1,4-diol-derived flame retardant compound 522, according to some embodiments of the present disclosure. In both reactions, 2-(hydroxymethyl)butane-1,4-diol 412 is reacted with a phosphorus-based flame-retardant molecule 204 or 206, catalytic dimethylaminopyridine (cat. DMAP), and/or a stoichiometric amount of an organic amine (e.g., triethylamine) in a dichloromethane (DCM) solution. When the reaction is carried out with an R-functionalized phosphorus-based compound 204, allyl- 306 or epoxy- 307 functionalized FR moieties are attached at the hydroxyl groups on 2-(hydroxymethyl)butane-1,4-diol 412. This reaction forms the trifunctionalized 2-(hydroxymethyl)butane-1,4-diol-derived flame retardant compound 520. This compound 520 is a flame retardant itaconic acid-based compound that can be polymerized or act as a cross-linker in another polymer. Its inclusion in a polymer, either as a monomer or a cross-linker, causes the polymer to be flame retardant.

If process 500-4 is carried out with a phenyl-substituted phosphorus-based compound 206, phenyl-substituted FR moieties are attached at the hydroxyl groups, and the phenyl-substituted 2-(hydroxymethyl)butane-1,4-diol-derived flame retardant compound 522 is formed. This compound 522 is a flame retardant itaconic acid-based small molecule, which can be blended with a polymer to impart flame retardancy.

Figure 5E:
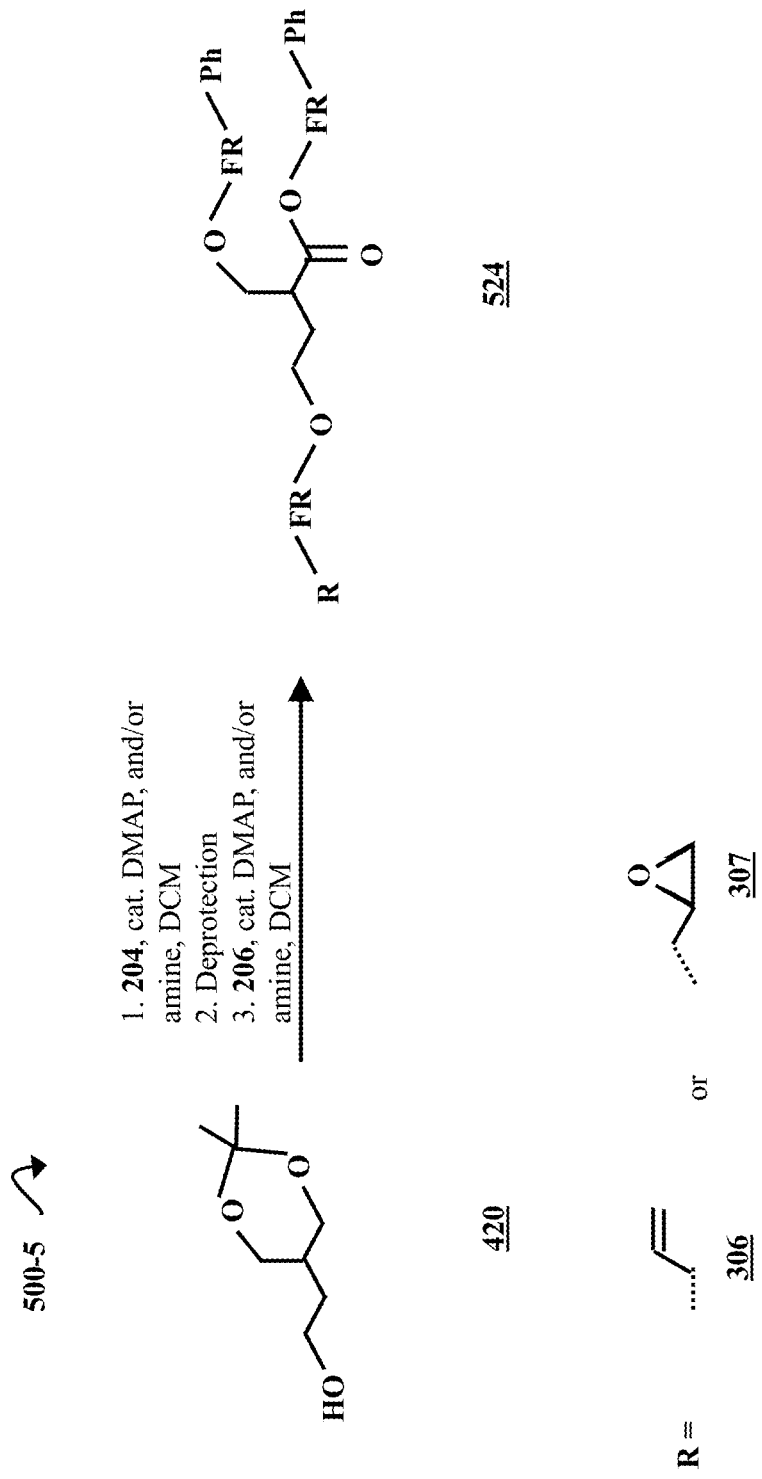
FIG. 5E is a chemical reaction diagram illustrating a process of forming a monofunctionalized 2-(2,2-dimethyl-1,3-dioxan-5-yl)ethanol-derived flame retardant compound, according to some embodiments of the present disclosure.

FIG. 5E is a chemical reaction diagram illustrating a process 500-5 of forming a monofunctionalized 2-(2,2-dimethyl-1,3-dioxan-5-yl)ethanol-derived flame retardant compound 524, according to some embodiments of the present disclosure. Process 500-5 is carried out in three steps. In the first step, itaconic acid-derived 2-(2,2-dimethyl-1,3-dioxan-5-yl)ethanol 420 is reacted with an R-functionalized phosphorus-based compound 204, catalytic dimethylaminopyridine (cat. DMAP), and/or a stoichiometric amount of an organic amine (e.g., triethylamine) in dichloromethane (DCM). This step attaches an R-functionalized FR moiety at the hydroxyl group on 2-(2,2-dimethyl-1,3-dioxan-5-yl)ethanol 420.

The second step is a ring-opening deprotection reaction. In this step, an acid such as p-toluenesulfonic acid (p-TsOH) or hydrochloric acid (HCl) is added in acetone to the reaction mixture. The acid addition exposes hydroxyl groups, which are then reacted in the third step with a phenyl-substituted phosphorus-based compound 206, cat. DMAP, and/or a stoichiometric amount of an organic amine in DCM. The third step attaches phenyl-substituted FR moieties to the newly exposed hydroxyl groups, and forms the monofunctionalized 2-(2,2-dimethyl-1,3-dioxan-5-yl) ethanol-derived flame retardant compound 524. In some embodiments, the phenyl-substituted flame retardant phosphorus-based compound 206 could be used in step one and the R-functionalized flame retardant phosphorus based compound 204 could be used in step two, producing a difunctionalized compound.

Figure 5F:
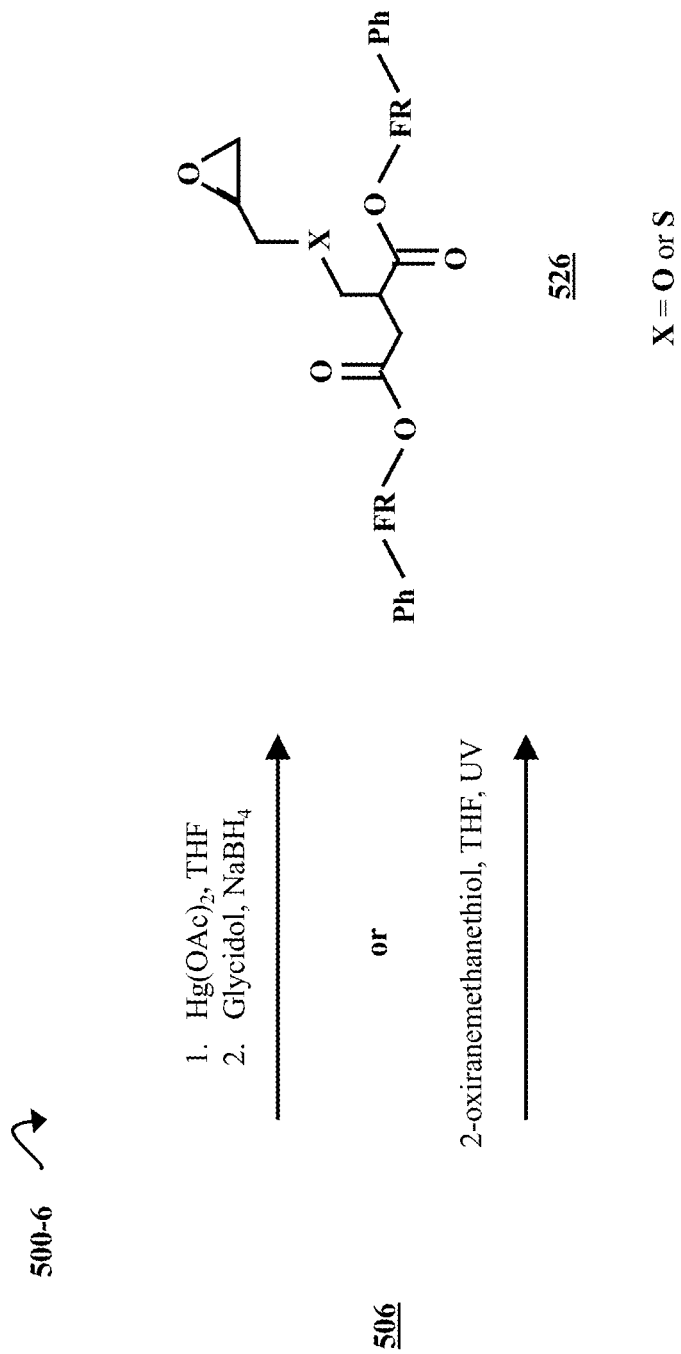
FIG. 5F is a chemical reaction diagram illustrating a process of forming a monofunctionalized itaconic acid-based flame retardant compound, according to some embodiments of the present disclosure.

FIG. 5F is a chemical reaction diagram illustrating a process 500-6 of forming a monofunctionalized itaconic acid-based flame retardant compound 526, according to some embodiments of the present disclosure. This monofunctionalized flame retardant compound 526 is synthesized from the phenyl-substituted itaconic acid-based flame retardant compound 506, which was discussed in greater detail with respect to FIG. 5A. Additionally, the flame retardant compound 526 has an ether- or thioether-linked epoxy functional group that is attached at the location of the vinyl moiety of the phenyl-substituted itaconic acid-based flame retardant compound 506 by either an oxygen (O) or sulfur (S) atom, symbolized by "X." When X is oxygen, the link is an ether, and when X is sulfur, the link is a thioether.

In order to form the ether-linked flame retardant compound 526, the phenyl-substituted itaconic acid-based flame retardant compound 506 is reacted in an oxymercuration reaction with mercury(II) acetate ($Hg(OAc)_2$) in tetrahydrofuran (THF), followed by glycidol and sodium borohydride ($NaBH_4$). In order to form the thioether-linked flame retardant compound 526, a thiol-ene reaction is carried out, wherein 2-oxiranemethanethiol and the phenyl-substituted itaconic acid-based flame retardant compound 506 are combined in THF, and exposed to ultraviolet (UV) light. The resulting monofunctionalized itaconic acid-based flame retardant compound 526 can be bound to polymer chains, or it can be polymerized, thereby forming a flame retardant polymer.

It should be noted that process 500-6 can also be carried out with the phenyl-substituted 2-methylenebutane-1,4-diol-derived flame retardant compound 514 instead of the phenyl-substituted itaconic acid-based flame retardant compound 506. This is because the phenyl-substituted 2-methylenebutane-1,4-diol-derived flame retardant compound 514 also has a reactive vinyl moiety. The substitution would result in a monofunctionalized methylenebutane-1,4-diol-derived flame retardant compound that is analogous to the monofunctionalized itaconic acid-based flame retardant compound 526. Likewise, process 500-6 could be carried out with the R-functionalized compounds 504 and 512, both of which have reactive vinyl moieties.

Figure 5G:
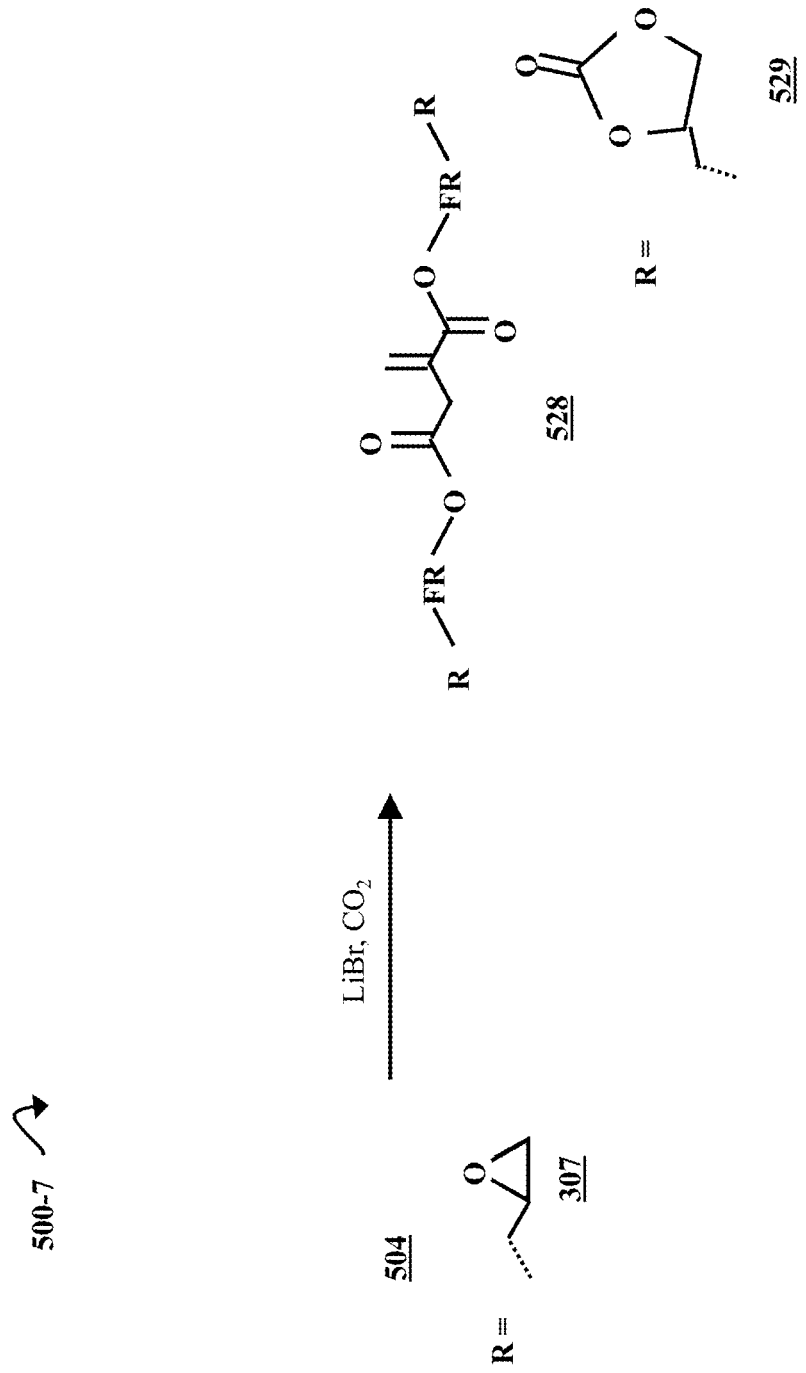
FIG. 5G is a chemical reaction diagram illustrating a process of forming a propylene carbonate-functionalized itaconic acid-based flame retardant compound, according to some embodiments of the present disclosure.

FIG. 5G is a chemical reaction diagram illustrating a process 500-7 of forming a propylene carbonate-functionalized itaconic acid-based flame retardant compound 528, according to some embodiments of the present disclosure. In this reaction, the difunctionalized itaconic acid-based flame retardant compound 504 with epoxy R groups 307 is combined with lithium bromide (LiBr). Carbon dioxide ($CO_2$) is added to the mixture, yielding the propylene carbonate-functionalized flame retardant itaconic acid-based compound 528. It should be noted that the reaction between the epoxy R groups 307, LiBr, and $CO_2$ can be carried out with any of the epoxy-functionalized compounds disclosed herein. This reaction converts any epoxy R groups 307 to propylene carbonate R groups 529.

FIG. 6A is a chemical reaction diagram illustrating a process 600-1 of forming phenyl-substituted thioether-linked flame retardant itaconic acid-based compounds 604, according to some embodiments of the present disclosure. The process 600-1 can be carried out under reaction conditions A, B, or C. Each of these reaction conditions is a thiol-ene reaction between the difunctionalized itaconic acid-based flame retardant compound 504 with allyl R groups 306 and a phenyl-substituted flame retardant thiol molecule 328, 336, or 348. Each thiol molecule binds to an allyl or vinyl group on the itaconic acid-based precursor 504. The syntheses and structures of the phenyl-substituted flame retardant thiol molecules are discussed in greater detail with regard to FIGS. 3C and 3D. The thiols provide phenyl-substituted thioether groups, which are also referred to as $E^1$ groups herein. The phenyl-substituted $E^1$-linked flame-retardant itaconic acid-based compounds 604 can be blended with polymers to impart flame retardancy.

Under thiol-ene reaction conditions A, the difunctionalized itaconic acid-based flame retardant compound 504 with allyl R groups 306 is reacted with the phenyl-substituted carboxylic acid-derived flame-retardant thiol molecule 328 under UV light in a methanol (MeOH) solution. The resulting $E^1$-linked flame-retardant itaconic acid-based compound 604 has thioether groups 608 that correspond to the carboxylic acid-derived flame-retardant thiol molecule 328.

Under thiol-ene reaction conditions B, the difunctionalized itaconic acid-based flame retardant compound 504 with allyl R groups 306 is reacted with the phenyl-substituted hydroxy-derived flame retardant thiol molecule 336 under UV light. The resulting $E^1$-linked flame-retardant itaconic acid-based compound 604 has phenyl-substituted thioether groups 612 that correspond to the hydroxy-derived flame retardant thiol molecule 336.

Under thiol-ene reaction conditions C, the difunctionalized itaconic acid-based flame retardant compound 504 with allyl R groups 306 is reacted with the phenyl-substituted amine-derived flame retardant thiol molecule 348 under UV light in a pH 9 methanol solution. The resulting $E^1$-linked flame-retardant itaconic acid-based compound 604 has phenyl-substituted thioether groups 616 that correspond to the amine-derived flame retardant thiol molecule 348.

FIG. 6B is a chemical reaction diagram illustrating a process 600-2 of forming trifunctionalized thioether-linked flame retardant itaconic acid-based compounds 624, according to some embodiments of the present disclosure. The process 600-2 is carried out under reaction conditions A, B, or C. Each of these reaction conditions is a thiol-ene reaction between the difunctionalized itaconic acid-based flame retardant compound 504 with allyl R groups 306 and a thiol molecule, which can be 3-mercaptopropionate 352, 2-mercaptoethanol 356, or cysteamine hydrochloride (HCl) 360. The thiols provide functionalized thioether groups, which are also referred to $E^2$ groups herein. Each thiol molecule reacts with an allyl or vinyl group on the itaconic acid-based precursor 504, forming trifunctionalized thioether-linked itaconic acid-based compounds 624. These compounds 624 can bind to polymers, and act as cross-linkers, causing the polymers to be flame retardant.

Under thiol-ene reaction conditions A, the difunctionalized itaconic acid-based flame retardant compound 504 with allyl R groups 306 is reacted with 3-mercaptopropionate 352 under UV light in a methanol (MeOH) solution. The resulting $E^2$-linked flame-retardant itaconic acid-based compound 624 has carboxylic acid-functionalized thioether groups 628 that correspond to the 3-mercaptopropionate 352. Under thiol-ene reaction conditions B, the difunctionalized itaconic acid-based flame retardant compound 504 with allyl 306 R groups is reacted with 2-mercaptoethanol 356 under UV light. The resulting $E^2$-linked flame-retardant itaconic acid-based compound 624 has hydroxyl-functionalized thioether groups 632 that correspond to the 2-mercaptoethanol 356. Under thiol-ene reaction conditions C, the difunctionalized itaconic acid-based flame retardant compound 504 with allyl R groups 306 is reacted with cysteamine HCl 360 under UV light in a pH 9 methanol solution. The resulting $E^2$-linked trifunctionalized flame-retardant itaconic acid-based compound 624 has amine-functionalized thioether groups 636 that correspond to the cysteamine HCl 360.

The reactions 600-1 and 600-2 between the vinyl groups and allyl R groups 306 on the difunctionalized itaconic acid-based flame retardant compound 504 and the thiol molecules 328, 336, 348, 352, 356, or 360 can be carried out with any of the allyl- and/or vinyl-functionalized compounds disclosed herein. The reactions attach the thioether groups 608, 612, 616, 628, 632, or 636 at the locations of the allyl and/or vinyl functional groups. This can result in different degrees of functionalization. For example, if thiol molecules are reacted with the phenyl-substituted 2-methylenebutane-1,4-diol-derived flame retardant compound 514, a thiol can bind to the vinyl functional group to form a phenyl-substituted (if the thiol is compound 328, 348, or 336) or monofunctionalized (if the thiol is compound 352, 356, or 360) thioether-linked 2-methylenebutane-1,4-diol-derived flame retardant compound. This reaction example is not illustrated herein. However, FIGS. 6C and 6D provide additional examples of thiol reactions.

FIG. 6C is a chemical reaction diagram illustrating a process 600-3 of forming phenyl-substituted thioether-linked flame retardant 2-(hydroxymethyl)butane-1,4-diol-derived compounds 640, according to some embodiments of the present disclosure. The process 600-3 is carried out under reaction conditions A, B, or C. These reaction conditions are substantially similar to those described with respect to process 600-1 in FIG. 6A. Each reaction is a thiol-ene reaction between the trifunctionalized 2-(hydroxymethyl)butane-1,4-diol-derived flame retardant compound 520 with allyl R groups 306 and a phenyl-substituted flame retardant thiol molecule 328, 336, or 348. Each thiol molecule binds to an allyl group on the 2-(hydroxymethyl)butane-1,4-diol-derived precursor 520. The resulting phenyl-substituted $E^1$-linked flame-retardant 2-(hydroxymethyl)butane-1,4-diol-derived compounds 640 can be blended with polymers to impart flame retardancy.

Figure 6D:
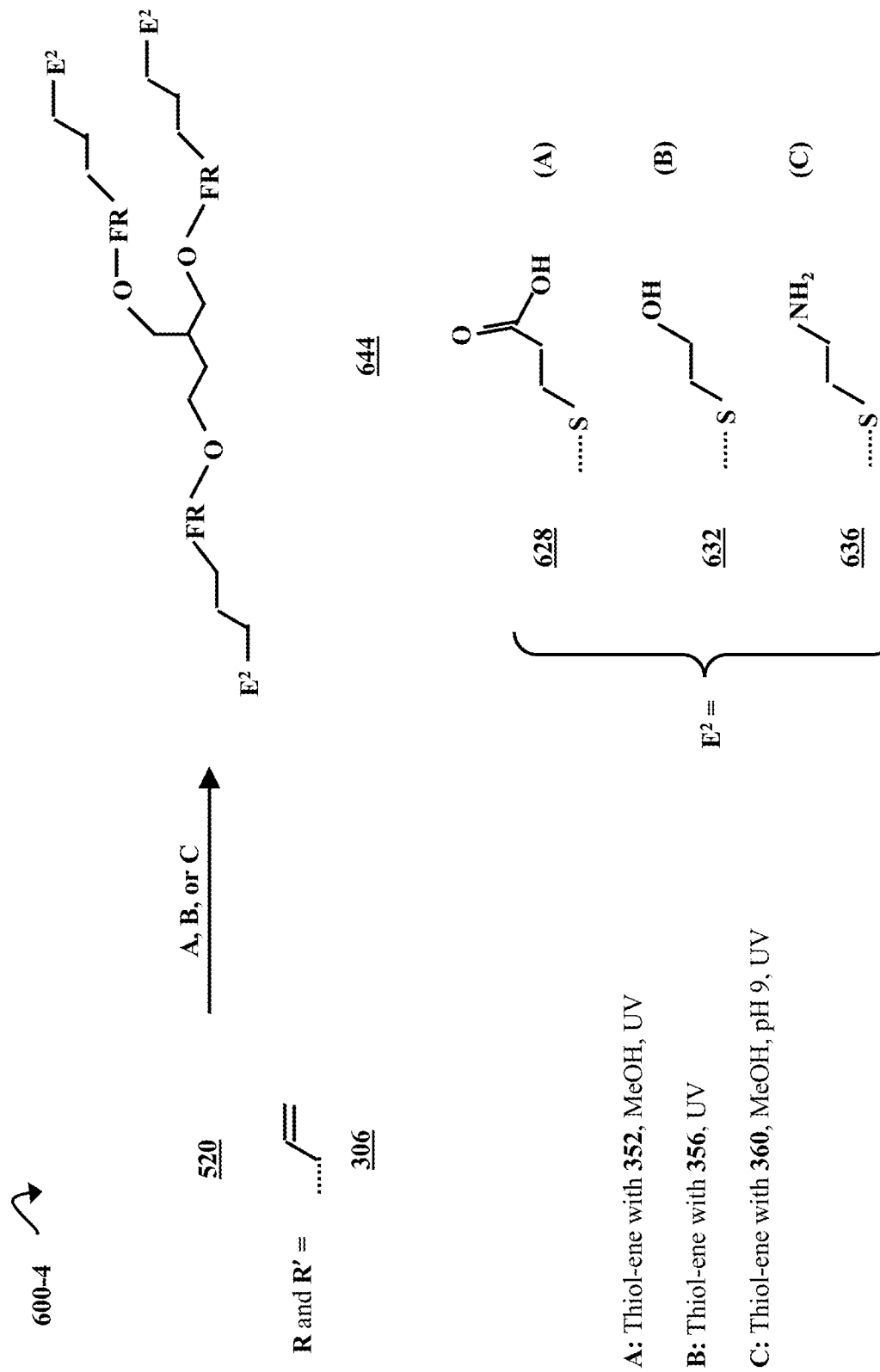
FIG. 6D is a chemical reaction diagram illustrating a process of forming trifunctionalized thioether-linked flame retardant itaconic acid-based compounds, according to some embodiments of the present disclosure.

FIG. 6D is a chemical reaction diagram illustrating a process 600-4 of forming trifunctionalized thioether-linked flame retardant itaconic acid-based compounds 644, according to some embodiments of the present disclosure. The process 600-4 is carried out under reaction conditions A, B, or C. These reaction conditions are substantially similar to those described with respect to process 600-2 in FIG. 6B. Each reaction is a thiol-ene reaction between the trifunctionalized 2-(hydroxymethyl)butane-1,4-diol-derived flame retardant compound 520 with allyl R groups 306 and a thiol molecule, which can be 3-mercaptopropionate 352, 2-mercaptoethanol 356, or cysteamine hydrochloride (HCl) 360. Each thiol molecule reacts with an allyl on the 2-(hydroxymethyl)butane-1,4-diol-derived precursor 520, forming trifunctionalized thioether-linked 2-(hydroxymethyl)butane-1,4-diol-derived compounds 644. These compounds 644 can bind to polymers, and act as cross-linkers, causing the polymers to be flame retardant.

The processes of forming the flame retardant itaconic acid-based compounds illustrated herein can be carried out with different combinations of phosphorus-based flame retardant molecules 204 and 206. In some embodiments, these processes can be carried out with either all phosphate-based flame retardant molecules (204-1 and/or 206-1) or all phosphonate-based flame retardant molecules (204-2 and/or 206-2). In other embodiments, a mixture of both phosphate- phosphonate-based flame retardant molecules can be used. Carrying out these processes with a mixture of phosphate- and phosphonate-based compounds (206-1/206-2 and/or 204-1/204-2) can result in the production of flame retardant itaconic acid-based monomers with both phosphoryl and phosphonyl FR groups.

However, in some instances, adding a mixture of phosphate- and phosphonate-based compounds (206-1/206-2 or 204-1/204-2) can result in the production of flame retardant itaconic acid-based monomers with all phosphoryl or all phosphonyl FR moieties. Additionally, adding a mixture of phosphate- and phosphonate-based compounds (206-1/206-2 or 204-1/204-2) to the reaction can yield a mixture of products that includes some combination of flame retardant itaconic acid-based monomers with either all phosphoryl or all phosphonyl FR groups and flame retardant itaconic acid-based monomers with both phosphoryl and phosphonyl FR groups.

Figure 7A:
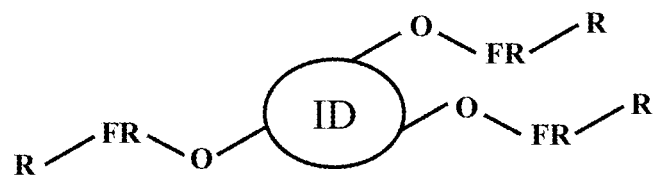
FIG. 7A is a diagrammatic representation of the structures of generic R-functionalized itaconic acid-based flame retardant monomers, according to some embodiments of the present disclosure.
Figure 7A:
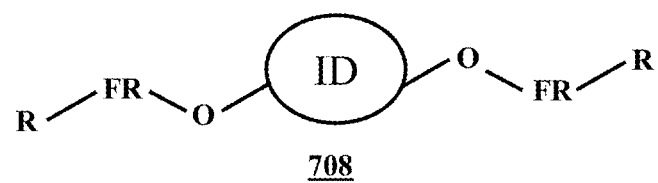
Figure 7A:
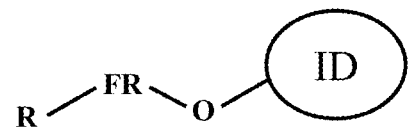

FIG. 7A is a diagrammatic representation of the structures 700 of generic R-functionalized itaconic acid-based flame retardant monomers 704, 708, and 712, according to some embodiments of the present disclosure. The monomers are trifunctionalized flame retardant itaconic acid-based compounds 704 (e.g., compounds 520), difunctionalized flame retardant itaconic acid-based compounds 708 (e.g., compounds 512 and 528), and monofunctionalized flame retardant itaconic acid-based compounds 712 (e.g., compounds 524 and 526). Examples of compounds represented by these structure 700 are discussed in greater detail with respect to FIGS. 5A-5G. The R-functionalized itaconic acid-based compounds 700 can be polymerized to form flame retardant itaconic acid-based polymers. Each structure shows only the ligands with R functional groups (e.g., allyl, epoxy, or propylene carbonate). An oval labeled "ID" represents the itaconic acid-derivative core of each monomer.

Figure 7B:
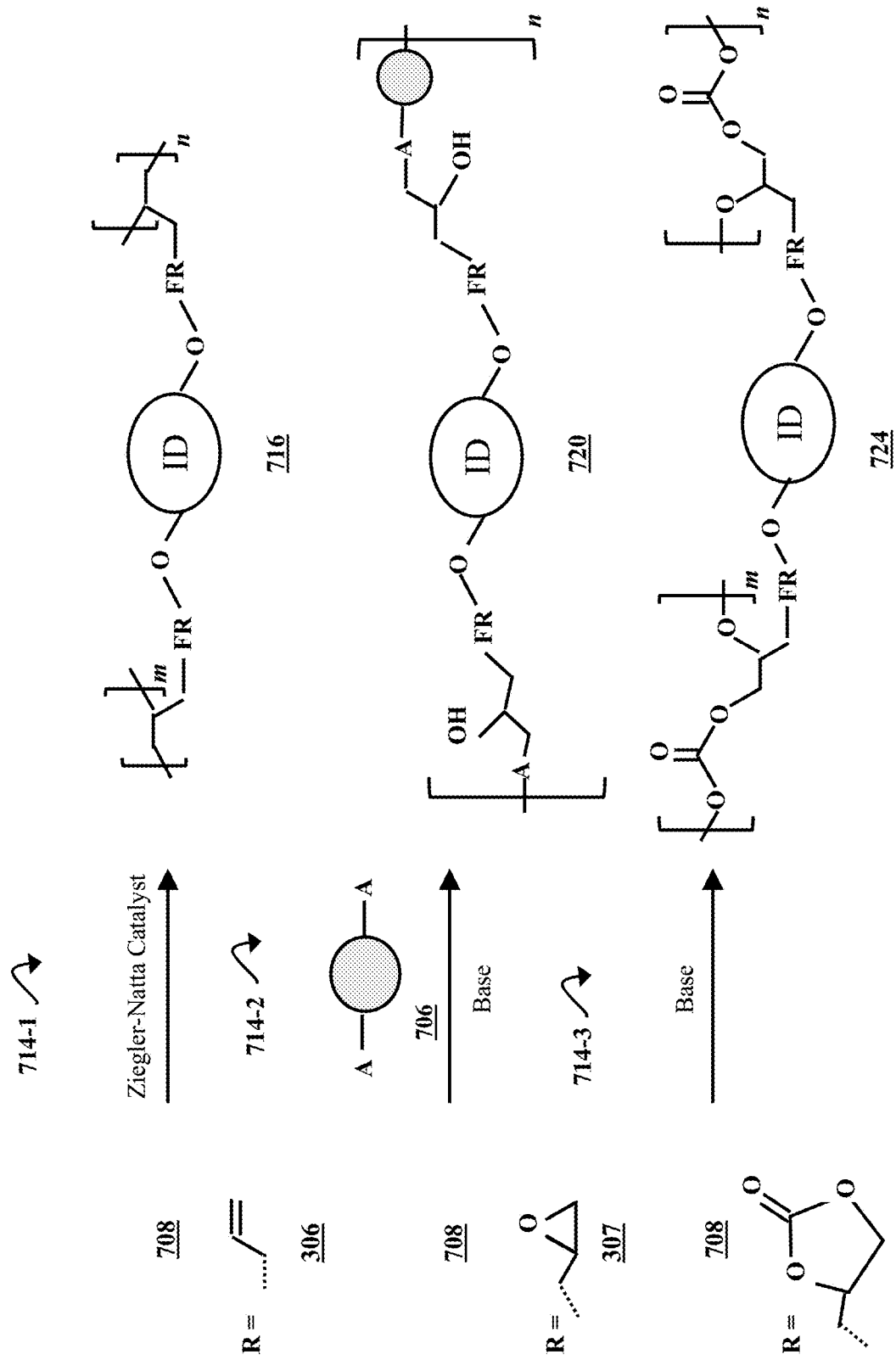
FIG. 7B is a chemical reaction diagram illustrating processes of synthesizing flame retardant itaconic acid-based polymers from flame retardant itaconic acid-based compounds, according to some embodiments of the present disclosure.

FIG. 7B is a chemical reaction diagram illustrating processes 714-1, 714-2, and 714-3 of synthesizing flame retardant itaconic acid-based polymers 716, 720, and 724 from flame retardant itaconic acid-based compounds, according to some embodiments of the present disclosure. The reactions illustrated herein are examples of polymers that can be synthesized from the flame retardant itaconic acid-based monomers, but other polymers can be produced as well (e.g., by changing reaction conditions, co-monomers, R groups, etc.).

Processes 714-1-714-3 illustrate the polymerization of difunctionalized flame retardant itaconic acid-based monomers 708 only. However, it should be noted that each of these polymerization reactions can also be carried out with the trifunctionalized flame retardant itaconic acid-based monomers 704. Additionally, processes 714-1 and 714-3 can be carried out with the monofunctionalized flame retardant itaconic acid-based monomers 712. Further, in some embodiments, the polymerization reactions are carried out with a combination of both difunctionalized flame retardant itaconic acid-based monomers 708 and trifunctionalized flame retardant itaconic acid-based monomers 704, both difunctionalized flame retardant itaconic acid-based monomers 708 and monofunctionalized flame retardant itaconic acid-based monomers 712, both trifunctionalized flame retardant itaconic acid-based monomers 704 and monofunctionalized flame retardant itaconic acid-based monomers 712, or a combination of monomers that includes tri-, di-, and monofunctionalized monomers in any ratio.

In process 714-1, allyl-derived flame retardant itaconic acid-based polymers 716 are formed from difunctionalized flame retardant itaconic acid-based compounds 708 having allyl R groups 306. The difunctionalized flame retardant itaconic acid-based compound 708 is reacted with a Ziegler-Natta catalyst. Ziegler-Natta catalysts catalyze the polymerization of 1-alkenes. Examples of these catalysts can include heterogeneous Ziegler-Natta catalysts based on titanium compounds and homogeneous Ziegler-Natta catalysts based on complexes of titanium, zirconium, or hafnium. Heterogeneous and homogeneous Ziegler-Natta catalysts can be used in combination with organoaluminum co-catalysts in some embodiments.

In process 714-2, epoxy-derived flame retardant itaconic acid-based polymers 720 are formed from difunctionalized flame retardant itaconic acid-based monomers 708 having epoxy R groups 307. The difunctionalized flame retardant itaconic acid-based compound 708 is reacted with a base and a second monomer 706. The second monomer 706 is a compound with at least two hydroxyl (OH) groups or at least two amino ($NH_2$) groups (e.g., a diol, polyol, diamine, polyamine, etc.) These compounds 706 are illustrated as a gray oval with attached A groups. The A group represents a hydroxyl group or an amino group. It should be noted that, while two A groups are illustrated herein, there are more than two A groups in some embodiments. Additionally, in some embodiments, the difunctionalized itaconic acid-based compound 708 having epoxy R groups 307 self-polymerizes under basic conditions. In these instances, the reaction does not include the second monomer 706.

In process 714-3, propylene carbonate-derived flame retardant itaconic acid-based polymers 724 are formed from difunctionalized flame retardant itaconic acid-based monomers having propylene carbonate R groups 529. The difunctionalized flame retardant itaconic acid-based monomer 708 having propylene carbonate R groups 529 is reacted in a ring-opening polymerization initiated by a base. Examples of bases that can be used as initiators can include potassium hydroxide (KOH), sodium hydroxide (NaOH), lithium hydroxide (LiOH), 1,8-diazabicyclo[5.4.0]undec-7-ene (DBU), triazabicyclodecene (TBD), etc.

In addition to the polymers illustrated in FIG. 7B, the flame retardant itaconic acid-based compounds disclosed herein can be used in the synthesis of other flame retardant polymers in some embodiments. An array of classes of flame retardant polymers can be made with different combinations of monomers. These polymerization processes are in accordance with polymer chemistry platforms that can include polyhydroxyurethanes, polycarbonates, polymers obtained by radical polymerization, polyurethanes, polyesters, polyacrylates, epoxy resins, polyimides, polyureas, polyamides, poly(vinyl-esters), etc.

One example of an application of polymers that incorporate flame retardant itaconic acid-based compounds is in plastics used in electronics hardware, such as integrated circuit packages. Additional applications can include acoustic dampening, cushioning, plastics, synthetic fibers, insulation, etc. The flame retardant itaconic acid-based compounds can also be used to make adhesives such as bio-adhesives, elastomers, thermoplastics, emulsions, thermosets, etc. Further, materials containing the flame retardant itaconic acid-based compounds can be incorporated into various devices with electronic components that can include printed circuit boards (PCBs), semiconductors, transistors, optoelectronics, capacitors, resistors, chip carriers, etc.

Resins for printed circuit boards (PCBs) can be made flame retardant by incorporating polymers that include itaconic acid-based flame retardant compounds. PCBs are electrical circuits that can be found in most types of electronic device, and they support and electronically connect electrical components in the device. PCBs are formed by etching a copper conductive layer laminated onto an insulating substrate. The insulating substrate can be a laminate comprising a resin and a fiber. Many resins in PCBs contain a polymer, such as an epoxy, a polyhydroxyurethane, a polycarbonate, a polyester, a polyacrylate, a polyimide, a polyamide, a polyurea, a poly(vinyl-ester), etc. Using polymers that incorporate the flame retardant itaconic acid-based compounds can prevent the PCB from catching fire when exposed to high temperature environments or electrical power overloads.

It should be noted that, in some embodiments, the compounds described herein can contain one or more chiral centers. These can include racemic mixtures, diastereomers, enantiomers, and mixtures containing one or more stereoisomer. Further, the disclosed compounds can encompass racemic forms of the compounds in addition to individual stereoisomers, as well as mixtures containing any of these.

The synthetic processes discussed herein and their accompanying drawings are not to be construed as limiting. One skilled in the art would recognize that a variety of synthetic reactions may be used that vary in reaction conditions, components, methods, etc., which ultimately generate one or both of flame retardant itaconic acid-based compounds and their corresponding polymer derivatives. In addition, the reaction conditions can optionally be changed over the course of a process. Further, in some embodiments, processes can be added or omitted while still remaining within the scope of the disclosure, as will be understood by a person of ordinary skill in the art.

What is claimed is:

1. A flame retardant itaconic acid-based compound with a formula of:

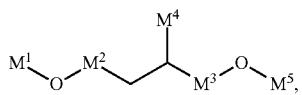

wherein $M^1$ is a moiety comprising:
an FR group, wherein the FR group is selected from the group consisting of a phosphoryl moiety and a phosphonyl moiety; and
a moiety attached to the FR group, wherein the moiety attached to the FR group is selected from the group consisting of a phenyl substituent and an R functional group, wherein the R functional group includes at least one moiety selected from the group consisting of an epoxy group, an allyl group, a propylene carbonate group, a carboxylic acid group, a hydroxyl group, and an amine group;
wherein $M^3$ is a moiety selected from the group consisting of a methylene bridge group and a carbonyl group;
wherein $M^2$ is a second methylene bridge group when $M^3$ is the methylene bridge group, and wherein $M^2$ is selected from the group consisting of the methylene bridge group and a second carbonyl group when $M^3$ is the carbonyl group;
wherein $M^4$ is a moiety selected from the group consisting of a vinyl group, an FR group attached to a phenyl substituent, and an FR group attached to an R functional group, wherein the R functional group includes at least one moiety selected from the group consisting of an epoxy group, an ally group, a propylene carbonate group, a carboxylic acid group, a hydroxyl group, and an amine group; and
wherein $M^5$ is a moiety selected from the group consisting of an FR group attached to a phenyl substituent and an FR group attached to an R functional group, wherein the R functional group includes at least one moiety selected from the group consisting of an epoxy group, an allyl group, a propylene carbonate group, a carboxylic acid group, a hydroxyl group, and an amine group.

2. The flame retardant itaconic acid-based compound of claim 1, wherein the phosphoryl moiety has the following formula:

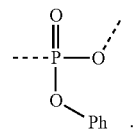

3. The flame retardant itaconic acid-based compound of claim 1, wherein the phosphonyl moiety has the following formula:

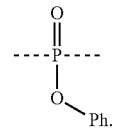

* * * * *